(12) United States Patent
Hoveyda et al.

(10) Patent No.: US 12,162,849 B2
(45) Date of Patent: Dec. 10, 2024

(54) SYNTHESIS OF 3-METHYL-1,2,4-THIADIAZOLE-5-CARBOHYDRAZIDE OR OF THE METHYL-d3 DEUTERATED FORM THEREOF

(71) Applicant: Ogeda SA, Brussels (BE)

(72) Inventors: Hamid Hoveyda, Brussels (BE); Guillaume Dutheuil, Vedrin (BE)

(73) Assignee: Ogeda SA, Vilvoorde (BE)

( * ) Notice: Subject to any disclaimer, the term of this patent is extended or adjusted under 35 U.S.C. 154(b) by 790 days.

(21) Appl. No.: 17/415,539

(22) PCT Filed: Dec. 20, 2019

(86) PCT No.: PCT/EP2019/086733
§ 371 (c)(1),
(2) Date: Jun. 17, 2021

(87) PCT Pub. No.: WO2020/128003
PCT Pub. Date: Jun. 25, 2020

(65) Prior Publication Data
US 2022/0056000 A1  Feb. 24, 2022

(30) Foreign Application Priority Data
Dec. 21, 2018  (EP) ..................... 18215106

(51) Int. Cl.
*C07D 285/04* (2006.01)
*C07D 285/08* (2006.01)

(52) U.S. Cl.
CPC .................. *C07D 285/08* (2013.01)

(58) Field of Classification Search
CPC ................................. C07D 285/04
See application file for complete search history.

(56) References Cited

U.S. PATENT DOCUMENTS

| 3,221,006 | A | 11/1965 | Moore et al. |
| 2010/0029650 | A1 | 2/2010 | Fang et al. |
| 2010/0160392 | A1 | 6/2010 | Joel et al. |
| 2011/0201605 | A1 | 8/2011 | Baumann et al. |
| 2012/0101086 | A1 | 4/2012 | Bailey et al. |
| 2014/0171411 | A1 | 6/2014 | Ledgard |

FOREIGN PATENT DOCUMENTS

| CN | 102653545 A | 9/2012 |
| CN | 117024374 A | 11/2023 |
| EP | 1975204 A2 | 10/2008 |
| EP | 3202763 A4 | 8/2017 |
| JP | 4-77477 A | 3/1992 |
| JP | 4-224570 A | 8/1992 |
| JP | 5031760 B2 | 9/2012 |
| JP | 2014-531464 A | 11/2014 |
| RU | 2021121378 A | 1/2023 |
| WO | 2007/100670 A1 | 9/2007 |
| WO | 2011/121137 A1 | 10/2011 |
| WO | 2013/050424 A1 | 4/2013 |
| WO | 2014/154895 A1 | 10/2014 |
| WO | 2014/154896 A1 | 10/2014 |
| WO | 2014/154897 A1 | 10/2014 |
| WO | 2016/046398 A1 | 3/2016 |
| WO | 2016/052439 A1 | 4/2016 |
| WO | 2019/012033 A1 | 1/2019 |

OTHER PUBLICATIONS

Goerdeler et al., Darstellung und Eigenschaften des 1.2.4- und des 1.3.4-Thiodiazols. Chemische Berichte, VCH. Jan. 1, 1956;89:1534-1543.
Verrier et al., Recent advances in direct C-H arylation: Methodology, selectivity and mechanism in oxazole series. Beilstein J Org Chem. 2011;7:1584-1601.
International Search Report and Written Opinion for Application No. PCT/EP2019/086733, dated Feb. 26, 2020, 14 pages.
Goerdeler et al., Uber 1.2.4-Thiodiazole, II. Mitteil.*): N-Methyl-Derivate der AMino-thio-diazole und Imino-thiodiazoline. Chemische Berichte. 1954;87(1):68-78.

(Continued)

*Primary Examiner* — John S Kenyon
(74) *Attorney, Agent, or Firm* — McCarter & English, LLP; Maria Laccotripe Zacharakis; Xin Zhang

(57) ABSTRACT

The present invention relates to a method of synthesis of compound (I), wherein $R^1$ represents methyl or methyl-d3, thus corresponding to 3-methyl-1,2,4-thiadiazole-5-carbohydrazide or to the methyl-d3 deuterated form thereof. These compounds are useful as key intermediates in the synthesis of pharmaceutical compounds, especially fezolinetant and deuterated fezolinetant.

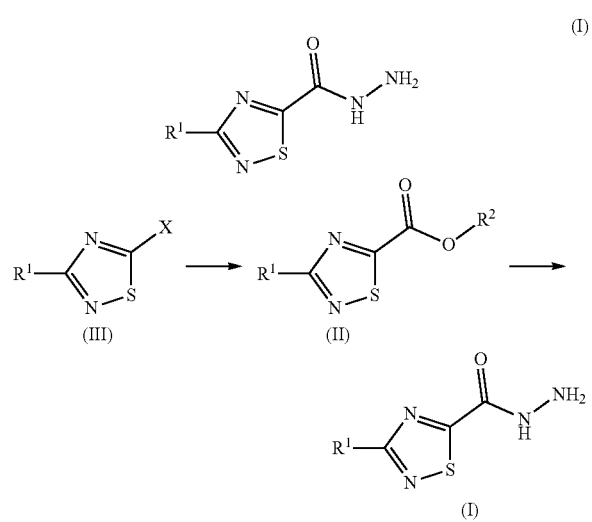

17 Claims, No Drawings

(56) References Cited

OTHER PUBLICATIONS

Goerdeler et al., Uber 1.2.4-Thiodiazole, VIII, Synthese von 5-Chlor-1.2.4-Thiodiazolen aus Perchlormethylmercaptan under Amidinen. Chemische Berichte. 1957;90:182-187.

Gurjar et al., Design, synthesis, in silico and in vitro screening of 1,2,4-thiadiazole analogues as non-peptide Inhibitors of beta-secretase. Bioorg Chem. Dec. 2014;57:90-98.

Hoveyda et al., Optimization of Novel Antagonists to the Neurokinin-3 Receptor for the Treatment of Sex-Hormone Disorders (Part II). ACS Med Chem Lett. May 19, 2015;6(7):736-40.

Hoveyda et al.. Discovery and optimization of novel antagonists to the human neurokinin-3 receptor for the treatment of sex-hormone disorders (Part I). J Med Chem. Apr. 9, 2015;58(7):3060-82.

Howe et al., Nitrile Sulfides. Synthesis of 1,2,4-Thiadiazoles. J Org Chem. 1974;39(7):962-964.

Reuman et al., Synthesis of a 5-((Aryloxy)methyl)-3-(4-(trifluoromethyl)phenyl)[1,2,4]thiadiazole Derivative: A Promising PPAR alpha, delta Agonist. Organic Process Research & Development. 2007;11:1010-1014.

Dox et al., Acetamidine Hydrochloride. Retrieved online at: http://www.orgsyn.org/demo.aspx?prep=CV1P0005. Organic Syntheses. 1928;8:1-3.

SYNTHESIS OF 3-METHYL-1,2,4-THIADIAZOLE-5-CARBOHYDRAZIDE OR OF THE METHYL-d3 DEUTERATED FORM THEREOF

REFERENCE TO RELATED APPLICATIONS

This application is a 35 U.S.C. § 371 national stage filing of International Application No. PCT/EP2019/086733, filed on Dec. 20, 2019, which in turn claims the benefit of European Patent Application No. 18215106.8, filed on Dec. 21, 2018. The entire contents of each of the foregoing applications are incorporated herein by reference.

FIELD OF INVENTION

The present invention relates to the field of chemical synthesis, and provides a method of synthesis of compound (I):

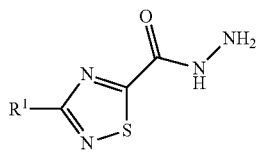

or a salt thereof, wherein $R^1$ represents methyl or methyl-d3, thus corresponding to 3-methyl-1,2,4-thiadiazole-5-carbohydrazide or to the methyl-d3 deuterated form thereof. These compounds are useful as key intermediates in the synthesis of pharmaceutical compounds, especially fezolinetant and deuterated fezolinetant.

BACKGROUND OF INVENTION

Fezolinetant was developed as selective antagonist of NK-3 receptor and is useful as therapeutic compound, particularly in the treatment and/or prevention of sex-hormone dependent diseases. Fezolinetant corresponds to (R)-(4-fluorophenyl)-(8-methyl-3-(3-methyl-1,2,4-thiadiazol-5-yl)-5,6-dihydro-[1,2,4]trizolo[4,3-a]pyrazin-7(8H)-yl)methanone and is described in WO2014/154895.

Deuterated fezolinetant, (R)-(4-fluorophenyl)-(8-methyl-3-(3-(methyl-d3)-1,2,4-thiadiazol-5-yl)-5,6-dihydro-[1,2,4]trizolo[4,3-a]pyrazin-7(8H)-yl)methanone, was also developed for the same purposes and is described in WO2019/012033.

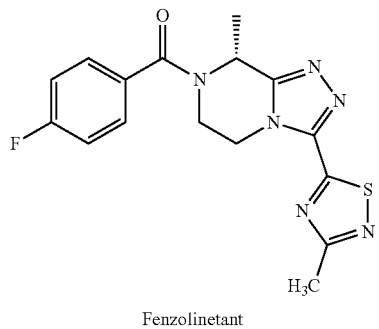

Fenzolinetant

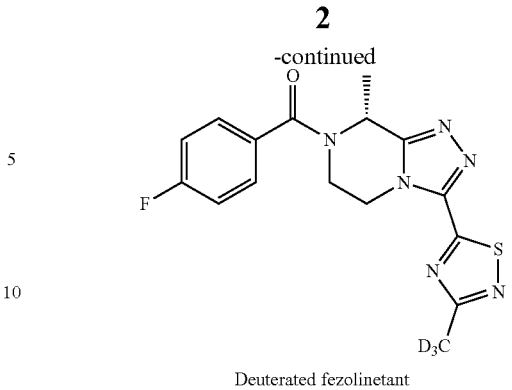

Deuterated fezolinetant

Methods of synthesis of fezolinetant, and deuterated fezolinetant are described in WO2014/154895 and WO2019/012033. These methods involve 3-methyl-1,2,4-thiadiazole-5-carbohydrazide or the deuterated form thereof as key intermediate (I):

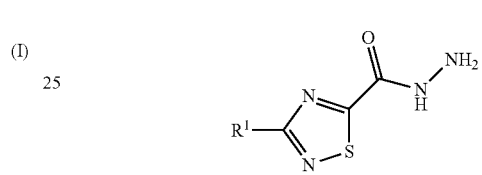

wherein $R^1$ represents methyl or methyl-d3.

A method of synthesis of the non-deuterated intermediate 3-methyl-1,2,4-thiadiazole-5-carbohydrazide (I-1) was disclosed in WO2013/050424, in which it is prepared from the corresponding methyl ester (II-1-a), this latter being prepared in one step from acetamide, chlorocarbonylsulfenyl chloride and methylcyanoformate:

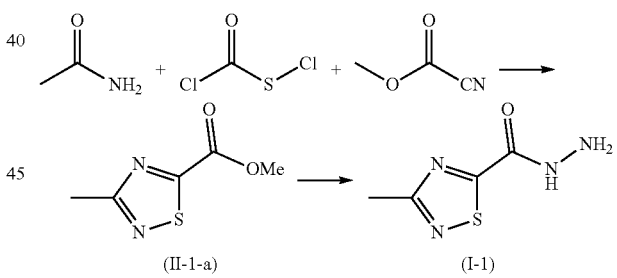

However, chlorocarbonylsulfenyl chloride and methylcyanoformate are hazardous reagents that lead to sourcing issues on scale and should be avoided for scale-up. Moreover, this route of synthesis leads to sulfur impurities that adversely impact quality of the final pharmaceutical product. Furthermore, even after optimization, the overall yield to intermediate (I-1) remains lower than 30%.

The corresponding deuterated intermediate 3-(methyl-d3)-1,2,4-thiadiazole-5-carbohydrazide (I-2) was obtained with the same method, as described in WO2019/012033, with the same drawbacks.

Therefore, there is a need for a safer, robust, scalable and more efficient synthesis of intermediate (I).

It is herein provided a method of synthesis of intermediate (I) from its corresponding ester (II), itself obtained by alkoxycarbonylation of the corresponding halogenated intermediate (III):

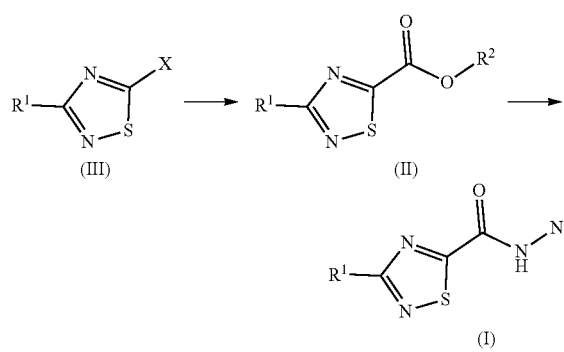

or salts thereof, wherein R¹ represents methyl or methyl-d3, R² represent an alkyl or arylalkyl group and X represents a halogen atom.

This type of alkoxycarbonylation was previously reported on few more robust 5-membered heterocycles such as thiophenes, furans, thiazoles, imidazole, oxazoles, pyrazoles and indoles. Nevertheless, it was never reported on less robust heterocycles (i.e. bearing more than 2 heteroatoms), much more prone to ring opening for instance such as thiadiazole rings, as in the present invention. In case of formation of opened intermediates of 1,2,4-thiadiazole, it would lead to very reactive intermediates (such as mercapto-amidine) and volatile side-products (especially in the case wherein R¹ is methyl) (see analogy for more robust oxazole in: Verrier et al., Beilstein J. Org. Chem., 2011, 7, 1584-1601; Bellina et al., Current Org. Chem., 2008, 12(9), 774-790 and Strotman et al., Org. Lett., 2010, 12, 3578-3581).

The process of the invention presents the advantage to involve no particularly hazardous chemistry of special reagent. Overall yields are very satisfying (more than 67%), even after scale-up, as evidenced in the experimental part below.

The starting halogenated compound of Formula (III) may be obtained by a Sandmeyer reaction from the amine compound of Formula (IV):

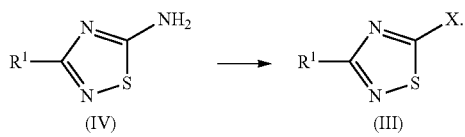

The invention further provides a new process for the synthesis of deuterated intermediate (IV). This process involves a Pinner reaction on deuterated acetonitrile (VII-2), which is first converted into Pinner salt (VI-2) (step a), and then in deuterated acetamidine (V-2) (step b), before forming the thiadiazole ring (step c) to provide compound (IV-2):

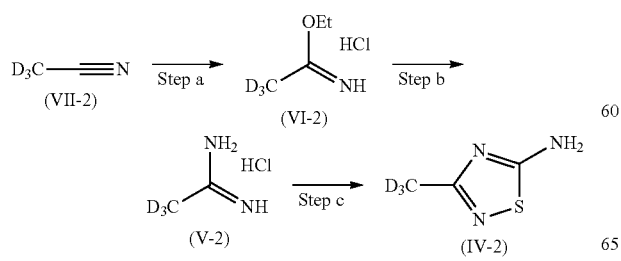

This process presents the advantage to be conducted with a very satisfying isotopic purity, as evidence in the experimental part below.

The invention also provides an alternative new process for the synthesis of deuterated intermediate (IV). This process involves the formation of the deuterated N-hydroxyacetamidine (IX-2) from deuterated acetonitrile (VII-2), which is then activated by tosylation to form intermediate (X-2), before forming the thiadiazole ring to provide compound (IV-2):

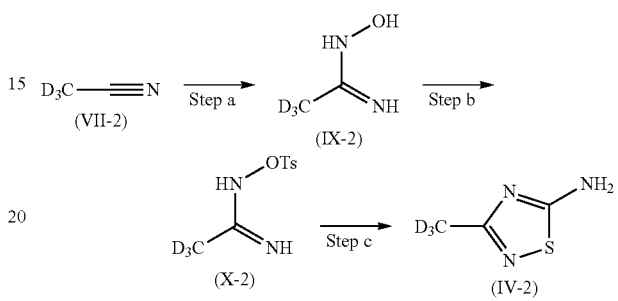

This process presents also the advantage to be conducted with a very satisfying isotopic purity.

SUMMARY

This invention thus relates to a process of manufacturing of a compound of Formula (I):

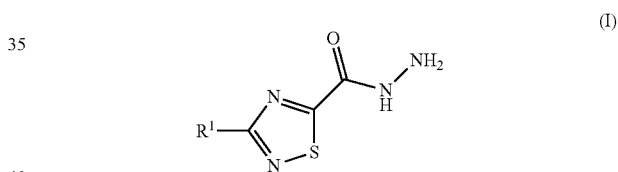

or a salt thereof, wherein R¹ represents methyl or methyl-d3;
said process comprising the following steps:
a) conducting an alkoxycarbonylation reaction on a compound of Formula (III):

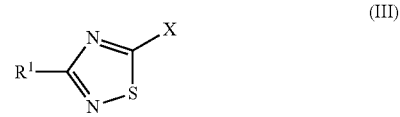

wherein X represents halo; and R¹ represents methyl or methyl-d3;
to obtain a compound of Formula (II):

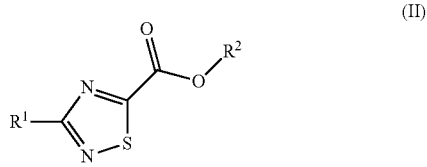

wherein R¹ represents methyl or methyl-d3; and R² represents alkyl or arylalkyl;
and b) forming the compound of Formula (I) by reacting compound of Formula (II) with hydrazine monohydrate.

In one embodiment, in the process of the invention, X represents bromo or iodo; preferably X represents bromo. In one embodiment, in the process of the invention, R² represents methyl or ethyl; preferably R² represents ethyl.

In one embodiment, the alkoxycarbonylation reaction of step a) is performed in presence of carbon monoxide, a palladium catalyst, a base and an alcohol solvent, and optionally in presence of an organophosphorus ligand.

In one embodiment, the palladium catalyst is Pd(OAc)₂, the organophosphorus ligand is 4,5-bis(diphenylphosphino)-9,9-dimethylxanthene (Xantphos), the base is sodium acetate and the solvent is selected from ethanol, methanol, and mixtures of methyl tert-butyl ether with ethanol or methanol. Preferably, step a) is performed in ethanol as solvent or in a mixture of ethanol and methyl tert-butyl ether. Preferably, step a) is performed at a temperature ranging from 50° C. to 150° C.; preferably from 63° C. to 67° C.; more preferably at about 65° C. In an embodiment, step a) is performed in presence of Fe(CO)₅.

In another embodiment, the palladium catalyst is bis(triphenylphosphine)palladium chloride (Pd(PPh₃)₂Cl₂), the base is triethylamine and the solvent is ethanol.

In one embodiment, the alkoxycarbonylation reaction of step a) is performed by lithium exchange by first contacting the compound of Formula (III) with an organolithium reagent; and then adding a chloroformate or a cyanoformate. Preferably, the organolithium reagent is n-hexyllithium and the chloroformate is an alkyl chloroformate, preferably ethyl chloroformate.

In one embodiment, the process of the invention comprises a preliminary step of Sandmeyer reaction on a compound of Formula (IV):

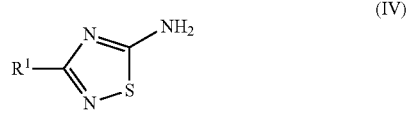

or a salt thereof, wherein R¹ represents methyl or methyl-d3;
leading to compound of Formula (III).

The Sandmeyer reaction may be performed in presence of sodium nitrite and hydrogen bromine, in an aqueous medium. Alternatively, the Sandmeyer reaction may be performed in presence of tert-butyl nitrite and iodine or in presence of potassium iodide and p-toluenesulfonic acid.

The invention also relates to a process of manufacturing of 3-(methyl-d3)-1,2,4-thiadiazole-5-amine (IV-2):

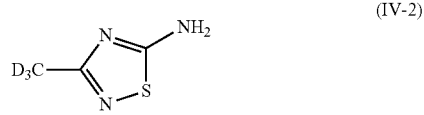

or a salt thereof,
comprising the following steps:
a) reacting d3-acetonitrile with ethanol in presence of HCl to form the Pinner salt of Formula (VI-2):

b) reacting Pinner salt (VI-2) with ammonia to form d3-acetamidine (V-2), or a salt thereof:

and
c1) reacting d3-acetamidine (V-2) with bromine, thiocyanate and sodium methoxide to afford compound of Formula (IV-2); or
c2) reacting d3-acetamidine (V-2) first with sodium hypochlorite (NaOCl) and then with thiocyanate to afford compound of Formula (IV-2).

Definitions

In the present invention, the following terms have the following meanings:

"About", preceding a figure, means plus or less 10% of the value of said figure.

"Alcohol solvent" refers to a substance that dissolves a solute (a chemically distinct liquid, solid or gas), resulting in a solution, and which is an alcohol, i.e. an organic compound comprising at least one hydroxyl functional group (—OH) linked to a carbon atom. Examples of alcohol solvents include methanol, ethanol and isopropyl alcohol.

"Alkoxycarbonylation reaction" refers to a chemical reaction of C—C bond formation enabling to introduce an alkoxycarbonyl moiety on a scaffold. By "alkoxycarbonyl moiety" it is made reference to a group —C(=O)—O-alkyl, wherein alkyl is as defined below, including cases wherein the alkyl is itself substituted, such as for example by an aryl group (i.e. forming an arylalkyl group), leading to —C(=O)—O-alkyl-aryl.

"Alkyl": refers to a hydrocarbyl radical of formula $C_nH_{2n+1}$ wherein n is a number greater than or equal to 1. Generally, alkyl groups of this invention comprise from 1 to 6 carbon atoms, preferably from 1 to 4. Alkyl groups may be linear or branched and may be substituted as indicated herein. Examples of alkyl groups are methyl, ethyl, n-propyl, i-propyl, butyl and its isomers (e.g. n-butyl, i-butyl and t-butyl); pentyl and its isomers, hexyl and its isomers.

"Aryl" refers to a polyunsaturated, aromatic hydrocarbyl group having a single ring (i.e. phenyl) or multiple aromatic rings fused together (e.g. naphtyl), or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Non-limiting examples of aryl comprise phenyl, biphenylyl, biphenylenyl, naphthalen-1- or -2-yl. In one embodiment, the aryl group is phenyl. Optionally, aryl groups may be substituted by one or more group(s), such as for example alkoxy groups. In a specific embodiment, the aryl group is substituted by 1 to 3 alkoxy group(s), preferably by 1 to 3 methoxy group(s).

"Arylalkyl" refers to a moiety aryl-alkyl-, wherein aryl and alkyl are as herein defined. Examples of arylalkyl groups include benzyl, 4-methoxybenzyl (PMB), 2,4-dimethoxybenzyl (DMB) and 2,4,6-trimethoxybenzyl (TMB).

"Carbonylation reaction" refers to a chemical reaction of C—C bond formation enabling to introduce a carbonyl moiety on a scaffold, for example a group —C(=O)—O—$R^2$, wherein $R^2$ is for example alkyl or arylalkyl.

"Chloroformate" refers to a reactant with the formula ROC(O)Cl, wherein R may represent alkyl or arylalkyl for example, leading to alkyl chloroformate and arylalkyl chloroformate, respectively.

"Cyanoformate" refers to a reactant with the formula ROC(O)CN, wherein R may represent alkyl or arylalkyl for example, leading to alkyl cyanoformate and arylalkyl cyanoformate, respectively.

"Halo" or "halogen" refers to fluoro, chloro, bromo or iodo. In the present invention, preferred halo groups are bromo and iodo.

"Methyl-d3" refers to the deuterated moiety —$CD_3$.

"Organolithium reagent" refers to an organometallic compound that contain carbon-lithium bonds. Examples of organolithium reagents include n-hexyllithium and n-butyllithium.

"Organophosphorus ligand" refers to organic compounds containing phosphorus, preferably phosphine ligands, i.e. compounds of formula $PR_3$ wherein R is an organic derivative. Examples of organophosphorus ligand include triphenylphosphine ($PPh_3$), tri-tert-butylphosphine ($PtBu_3$), 4,5-bis(diphenylphosphino)-9,9-dimethylxanthene (Xantphos), 2,2'-bis(diphenylphosphino)-1,1'-binaphthyl (BINAP), 1,3-bis(diphenylphosphino)propane (dppp) and di(1-adamantyl)-n-butylphosphine (cataCXium® A).

"Palladium catalyst" refers to a palladium complex able to catalyze a reaction. Examples of palladium catalysts include: palladium acetate ($Pd(OAc)_2$), palladium chloride ($PdCl_2$), tris(dibenzylideneacetone)dipalladium, bis(dibenzylideneacetone)palladium and bis(triphenylphosphine)palladium chloride ($Pd(PPh_3)_2Cl_2$). Palladium catalyst includes pre-catalysts, that become activated in situ, such as for example $Pd(PPh_3)_2Cl_2$ which is reduced to a Pd(0) complex or transmetalated to a Pd(II) aryl complex before it participates in the catalytic cycle.

"Pinner salt" refers to the product of the reaction of a nitrile with an alcohol, i.e. an imino ester salt (alkyl imidate salt).

"Sandmeyer reaction" refers to a chemical reaction used to synthesize aryl or heteroaryl halides from aryl or heteroaryl diazonium salts, by radical-nucleophilic aromatic substitution.

"Thiocyanate" refers to the anion [SCN]$^-$. It may be used as a salt, with counterions such as for example potassium or sodium.

"Tosylation" refers to a reaction enabling the introduction of a p-toluenesulfonyl group (also named tosyl group) on a hydroxyl moiety. In a preferred embodiment, tosylation is performed using p-toluenesulfonyl chloride.

DETAILED DESCRIPTION

Synthesis of Compound (I)

This invention relates to a process of manufacturing of a compound of Formula (I):

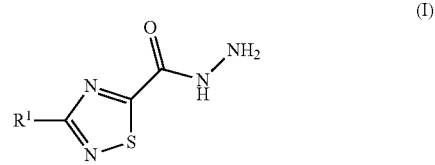

or a salt thereof, wherein $R^1$ represents methyl or methyl-d3;

said process comprising the following steps:
a) conducting an alkoxycarbonylation reaction on a compound of Formula (III):

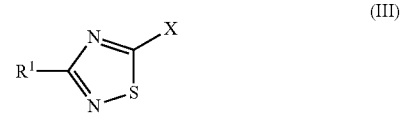

wherein X represents halo; and $R^1$ represents methyl or methyl-d3;
to obtain a compound of Formula (II):

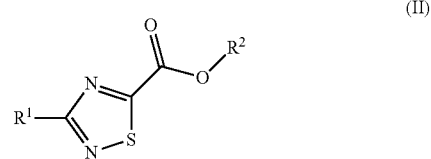

wherein $R^1$ represents methyl or methyl-d3; and $R^2$ represents alkyl or arylalkyl;
and
b) forming the compound of Formula (I) by reacting compound of Formula (II) with hydrazine monohydrate.

The final compound or the intermediates used in the processes of the invention may be in the form of salts, including acid addition and base salts. In one embodiment, the salts are pharmaceutically acceptable salts. Suitable acid addition salts are for examples acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are for examples aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts.

Step a)—Alkoxycarbonylation

In one embodiment, in compound of Formula (III), X represents bromo or iodo. In a preferred embodiment, in compound of Formula (III), X represents bromo. In another embodiment, in compound of Formula (III), X represents iodo.

In one embodiment, in compound of Formula (II), $R^2$ represents a C1-C4 alkyl group, preferably methyl or ethyl, more preferably $R^2$ represents ethyl. In another embodiment, in compound of Formula (II), $R^2$ represents an arylalkyl group, preferably benzyl, 4-methoxybenzyl (PMB), 2,4-dimethoxybenzyl (DMB) or 2,4,6-trimethoxybenzyl (TMB).

Alcoxycarbonylation with CO/Pd

In one embodiment, the alkoxycarbonylation reaction of step a) is performed in presence of carbon monoxide. In one embodiment, carbon monoxide is used at a pressure ranging from 1 to 20 bar, preferably from 3.5 to 8.5 bar, more preferably from 4 to 5 bar.

In one embodiment, the alkoxycarbonylation reaction of step a) is performed in presence of a palladium catalyst. In one embodiment, the palladium catalyst is for example selected from palladium acetate (Pd(OAc)$_2$), palladium chloride (PdCl$_2$), tris(dibenzylideneacetone)dipalladium, bis(dibenzylideneacetone)palladium and bis(triphenylphosphine)palladium chloride (Pd(PPh$_3$)$_2$Cl$_2$). In a preferred embodiment, the palladium catalyst is palladium acetate. In a preferred embodiment, the palladium catalyst is bis(triphenylphosphine)palladium chloride.

In one embodiment, the alkoxycarbonylation reaction of step a) is performed in presence of an organophosphorus ligand. In one embodiment, the organophosphorus ligand is selected from triphenylphosphine (PPh$_3$), tri-tert-butylphosphine (PtBu$_3$), 4,5-bis(diphenylphosphino)-9,9-dimethylxanthene (Xantphos), 2,2'-bis(diphenylphosphino)-1,1'-binaphthyl (BINAP), 1,3-bis(diphenylphosphino)propane (dppp) and di(1-adamantyl)-n-butylphosphine (cataCXium® A). In a preferred embodiment, the organophosphorus ligand is 4,5-bis(diphenylphosphino)-9,9-dimethylxanthene (Xantphos). In another embodiment, the organophosphorus ligand is triphenylphosphine (PPh$_3$).

Alternatively, depending on the palladium catalyst, the alkoxycarbonylation reaction of step a) is performed in absence of organophosphorus ligand. This is for example the case when using bis(triphenylphosphine)palladium chloride (Pd(PPh$_3$)$_2$Cl$_2$) as palladium catalyst.

In one embodiment, the alkoxycarbonylation reaction of step a) is performed in presence of a base. In one embodiment, the base is selected from sodium acetate (NaOAc), N,N-diisopropylethylamine (DIPEA), lutidine, N-methylmorpholine (NMM), tributylamine, triethylamine (TEA) and mixtures thereof. In a preferred embodiment, the base is sodium acetate. In one embodiment, the base is used under dried form.

In one embodiment, step a) is performed in a solvent adapted to obtain pursued $R^2$ moiety. In an embodiment, step a) is performed in an alcohol, preferably methanol or ethanol. In an embodiment, step a) is performed in a mixture of an alcohol solvent and methyl tert-butyl ether (MTBE), such as for example a mixture of MTBE with methanol or ethanol. In one embodiment, when $R^2$ is ethyl, step a) is performed in ethanol or in a mixture of ethanol and MTBE. The solvent may be dry or not dry. In one embodiment, from 2 to 30 volumes of solvent are used, preferably from 5 to 10 volumes, more preferably about 10 volumes.

In one embodiment, compound of Formula (III) is used at a concentration ranging from 0.01 M to 1 M, preferably from 0.1 M to 0.5 M, more preferably from 0.2 M to 0.4 M.

In one embodiment, the number of molar equivalents of base (such as sodium acetate) is ranging from 1 to 3 with respect to compound (III); preferably from 1.1 to 2; more preferably from 1.1 to 1.5, more preferably about 1.3 equivalents.

In one embodiment, the number of molar equivalents of palladium catalyst (such as palladium acetate) is ranging from 0.003 to 0.1 with respect to compound (III); preferably from 0.005 to 0.05; more preferably from 0.005 to 0.01, more preferably about 0.005 equivalents.

In one embodiment, the number of molar equivalents of organophosphorus ligand (such as Xantphos) is ranging from 0.003 to 0.2 with respect to compound (III); preferably from 0.005 to 0.15; more preferably from 0.005 to 0.05, more preferably about 0.005 equivalents.

In one embodiment, step a) is performed at a temperature ranging from 50° C. to 150° C., preferably from 63° C. to 67° C., more preferably at about 65° C. Alternatively, step a) may be performed at a temperature ranging from 90° C. to 120° C., preferably from 100° C. to 110° C.

In one embodiment, step a) is performed for a period of time of at least 3 hours, preferably ranging from 10 hours to 48 hours, preferably from 15 to 40 hours. In one embodiment, step a) is performed for about 19 hours. In one embodiment, step a) is performed for about 30 hours. In one embodiment, step a) is performed for about 37 hours. The duration of the reaction is adapted to the scale of amounts involved in the reaction.

In one embodiment, after completion, the resulting product is extracted with dichloromethane, tert-butyl methyl ether, or methyl-cyclohexane, preferably with methyl-cyclohexane.

In one embodiment, resulting product (II) may be purified by distillation.

In one embodiment, the alkoxycarbonylation reaction of step a) is performed in presence of carbon monoxide, a palladium catalyst, an organophosphorus ligand, a base and an alcohol solvent. In one embodiment, the palladium catalyst is palladium acetate, the organophosphorus ligand is 4,5-bis(diphenylphosphino)-9,9-dimethylxanthene (Xantphos), the base is sodium acetate and the solvent is ethanol or a mixture of MTBE and ethanol. In another embodiment, the palladium catalyst is palladium acetate, the organophosphorus ligand is triphenylphosphine (PPh$_3$), the base is triethylamine and the solvent is ethanol or a mixture of MTBE and ethanol.

In another embodiment, the alkoxycarbonylation reaction of step a) is performed in presence of carbon monoxide, a palladium catalyst, a base and an alcohol solvent. In one embodiment, the palladium catalyst is bis(triphenylphosphine)palladium chloride (Pd(PPh$_3$)$_2$Cl$_2$), the base is triethylamine and the solvent is ethanol or a mixture of MTBE and ethanol.

Alkoxycarbonylation with Fe(CO)$_5$

In one embodiment, the alkoxycarbonylation reaction of step a) is performed in presence of Fe(CO)$_5$.

In one embodiment, the alkoxycarbonylation reaction of step a) is performed in presence of carbon monoxide, a palladium catalyst, an organophosphorus ligand, a base and Fe(CO)$_5$ in an alcohol solvent. Embodiments detailed above regarding alkoxycarbonylation conditions and especially regarding these components also apply when used with Fe(CO)$_5$.

In one embodiment, the number of molar equivalents of Fe(CO)$_5$ is ranging from 0.01 to 0.5 with respect to compound (III); preferably from 0.05 to 0.2; more preferably from about 0.01 equivalents.

Alkoxycarbonylation Via Li-Exchange

In one embodiment, the alkoxycarbonylation reaction of step a) is performed by lithium exchange.

In one embodiment, the alkoxycarbonylation reaction of step a) is performed by first contacting the compound of Formula (III) with an organolithium reagent; and then by adding a chloroformate or a cyanoformate, to obtain the compound of Formula (II).

In one embodiment, the organolithium reagent is selected from n-hexyllithium and n-butyllithium; preferably the organolithium reagent is n-hexyllithium.

In one embodiment, the chloroformate is selected from alkyl chloroformate and arylalkyl chloroformate; preferably the alkyl chloroformate is selected from ethyl chloroformate, methyl chloroformate and s-butyl chloroformate, and the arylalkyl chloroformate is for example benzyl chloroformate; more preferably the chloroformate is an alkyl chloroformate such as ethyl chloroformate.

In one embodiment, the cyanoformate is selected from alkyl cyanoformate and arylalkyl cyanoformate; preferably the alkyl cyanoformate is selected from ethyl cyanoformate, methyl cyanoformate and t-butyl cyanoformate, and the arylalkyl cyanoformate is for example benzyl cyanoformate; more preferably the cyanoformate is an alkyl cyanoformate such as ethyl cyanoformate.

In one embodiment, the number of molar equivalents of organolithium reagent (preferably hexyllithium) is ranging from 1 to 2 with respect to compound (III); preferably from 1 to 1.5 more preferably from about 1.1 equivalents.

In one embodiment, the number of molar equivalents of chloroformate (preferably ethyl chloroformate) is ranging from 1 to 10 with respect to compound (III); preferably from 4 to 8 more preferably from about 6 equivalents.

In one embodiment, the lithium exchange is performed under inert atmosphere.

In one embodiment, the lithium exchange is performed is a dry solvent such as methyltetrahydrofuran (MeTHF), tetrahydrofuran (THF), tert-butyl methyl ether (TBME), n-hexane and mixtures thereof, preferably in methyltetrahydrofuran.

In one embodiment, the lithium exchange is performed at a temperature lower than 0° C., preferably at about −65° C.

In one embodiment, the resulting compound of Formula (II) may be purified by distillation.

Step b)—Formation of the Acyl Hydrazine (Step b)

In step b), the compound of Formula (I) is formed by reacting compound of Formula (II) with hydrazine, preferably hydrazine monohydrate.

In one embodiment, the number of molar equivalents of hydrazine is ranging from 1 to 2 with respect to compound of Formula (II); preferably from 1.1 to 1.2; more preferably about 1.14 equivalents.

In one embodiment, step b) is conducted in a solvent selected from methanol, ethanol and isopropyl alcohol. In a preferred embodiment, the solvent is isopropyl alcohol. In another preferred embodiment, the solvent is ethanol.

In one embodiment, step b) is conducted at a temperature lower than 10° C., preferably ranging from 0° C. to 5° C.

In one embodiment, step b) is conducted for a period of time of at least 30 min, preferably at least 1 hour, preferably ranging from 1 hour to 48 hours, more preferably from 1 hour to 24 hours.

In one embodiment, after completion, compound of Formula (I) is recovered as a solid and may be washed with a solvent such as methanol or isopropylalcohol.

Sandmeyer Reaction (Preliminary Step)

In one embodiment, the process of the invention comprises a preliminary step of Sandmeyer reaction on a compound of Formula (IV) leading to the compound of Formula (III). For example, when X is Br, compound (III-1-a) may be obtained using the method reported by Goerdeler et al. in Chem. Ber., 1956, 89, 1534-1540 or in US2007/0078155.

In one embodiment, the halide compound of Formula (III) is obtained by a Sandmeyer reaction, from the compound of Formula (IV):

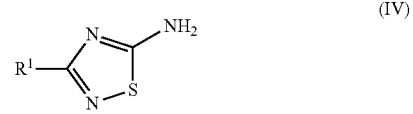

or a salt thereof, wherein R$^1$ represents methyl or methyl-d3.

In one embodiment, the Sandmeyer reaction is performed by first forming the diazonium salt from the amine, in presence of nitrous acid, generated in situ, followed by its displacement with a halide anion as nucleophile.

In one embodiment, the bromination by Sandmeyer reaction is performed in presence of sodium nitrite (NaNO$_2$) and hydrogen bromine (HBr), preferably in aqueous medium. In such case, in compound of formula (III), X is bromo.

In one embodiment, the number of molar equivalents of hydrogen bromine is ranging from 1 to 5 with respect to compound (IV); preferably from 2 to 4; more preferably about 3 equivalents.

In one embodiment, the number of molar equivalents of sodium nitrite is ranging from 1.15 to 4 with respect to compound (IV); preferably from 1.5 to 2; more preferably about 1.5 equivalents.

In one embodiment, the Sandmeyer reaction is performed at a temperature ranging from room temperature to 60° C., preferably from 35° C. to 50° C., more preferably from about 40° C. to about 45° C.

In one embodiment, the Sandmeyer reaction is performed for a period of time of at least 30 min, preferably ranging from 30 minutes to 22 hours, preferably from 30 minutes to 2 hours, more preferably for about 1 hour.

In one embodiment, the Sandmeyer reaction is performed in presence of 1 molar equivalent of amine compound of Formula (IV), 3 molar equivalents of hydrogen bromine and 1.5 molar equivalents of sodium nitrite, in water. Preferably, the reaction is conducted at a temperature of about 40° C. Preferably, the reaction is conducted in 5 volumes of water.

In one embodiment, after completion, the product is recovered by extraction with dichloromethane. Preferably, the organic phase is neutralized using a NaOH solution.

In another embodiment, the bromination by Sandmeyer reaction is performed in presence of tert-butyl nitrite (tBuONO) and CuBr$_2$. In such case, in compound of formula (III), X is bromo.

In one embodiment, the number of molar equivalents of CuBr$_2$ is ranging from 1 to 3 with respect to compound (IV); preferably from 1 to 1.1; more preferably about 1.03 equivalents.

In one embodiment, the number of molar equivalents of tert-butylnitrite is ranging from 1 to 3 with respect to compound (IV); preferably from 1 to 2; more preferably about 1.5 equivalents.

In one embodiment, the Sandmeyer reaction is performed at a temperature ranging from 0° C. to 40° C., preferably from 0° C. to room temperature.

In one embodiment, the Sandmeyer reaction is performed for a period of time of at least 30 min, preferably ranging from 30 minutes to 10 hours, preferably from 30 minutes to 5 hours, more preferably from 2 hours to 3 hours.

In one embodiment, the Sandmeyer reaction is performed in presence of 1 molar equivalent of amine compound of Formula (IV), 1.03 molar equivalents of CuBr$_2$ and 1.5 molar equivalents of tert-butylnitrite, in acetonitrile. Preferably, the reaction is first conducted at a temperature of about 0-5° C. and then at room temperature.

In one embodiment, after completion, the product is recovered by extraction with tert-butyl methyl ether.

In another embodiment, the iodination by Sandmeyer reaction is performed in presence of tert-butyl nitrite (tBuONO) and iodine. In such case, in compound of formula (III), X is iodo. Preferably such reaction is performed in a solvent such as for example acetonitrile.

In one embodiment, the number of molar equivalents of iodine is ranging from 1 to 3 with respect to compound (IV); preferably from 1 to 2; more preferably about 1 equivalent.

In one embodiment, the number of molar equivalents of tert-butyl nitrite is ranging from 1 to 5 with respect to compound (IV); preferably from 3 to 5; more preferably about 4 equivalents.

In one embodiment, the Sandmeyer reaction is performed at a temperature ranging from room temperature to reflux.

In one embodiment, the Sandmeyer reaction is performed for a period of time of at least 30 min, preferably ranging from 30 minutes to 5 hours, preferably from 30 minutes to 2 hours, more preferably for about 1 hour.

In one embodiment, the Sandmeyer reaction is performed in presence of 1 molar equivalent of amine compound of Formula (IV), 1 molar equivalents of iodine and 4 molar equivalents of tert-butyl nitrite.

In one embodiment, after completion, the excess of iodine is quenched, preferably by addition of Na$_2$SO$_3$. Then, the resulting compound may be extracted using methyl-tert-butyl ether.

In another embodiment, the iodination by Sandmeyer reaction is performed in presence of sodium nitrite (NaNO$_2$), potassium iodide (KI) and p-toluenesulfonic acid (TsOH). In such case, in compound of formula (III), X is iodo.

In one embodiment, the number of molar equivalents of potassium iodide is ranging from 1 to 4 with respect to compound (IV); preferably from 2 to 3; more preferably about 2.6 equivalent.

In one embodiment, the number of molar equivalents of sodium nitrite is ranging from 1 to 3 with respect to compound (IV); preferably from 1.5 to 2.5; more preferably about 2 equivalent.

In one embodiment, the number of molar equivalents of p-toluenesulfonic acid is ranging from 1 to 6 with respect to compound (IV); preferably from 3 to 4; more preferably about 3.5 equivalent.

In one embodiment, the Sandmeyer reaction is preferably performed at room temperature.

In one embodiment, the Sandmeyer reaction is performed for a period of time of at least 1 hour, preferably ranging from 1 hour to 24 hours, preferably for about 12 hours.

In one embodiment, the Sandmeyer reaction is performed in presence of 1 molar equivalent of amine compound of Formula (IV), 2.6 molar equivalents of potassium iodide, about 2 molar equivalents of sodium nitrite and 3.5 molar equivalents of p-toluenesulfonic acid.

Synthesis of Deuterated Compound (IV-2)

The non-deuterated intermediate (IV-1), i.e. compound of Formula (IV) wherein R$^1$ is methyl, also referred to as AMTD, is commercially available or may be obtained by methods known by one skilled in the art.

For the corresponding deuterated intermediate (IV-2), i.e. compound of Formula (IV) wherein R$^1$ is methyl-d3, it is not predictable from non-deuterated routes of synthesis, what isotopic purity can be achieved. It is herein provided a method of synthesis of intermediate (IV-2) leading to very high isotopic purities, namely an overall isotopic purity of more than 90%, more preferably of more than 95%.

d3-Acetamidine Route

The invention thus further relates to a process of manufacturing of 3-(methyl-d3)-1,2,4-thiadiazole-5-amine (IV-2):

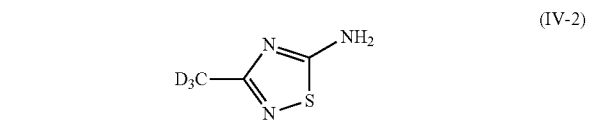

or a salt thereof,
comprising the following steps:
a) reacting d3-acetonitrile with ethanol in presence of HCl to form the Pinner salt of Formula (VI-2):

b) reacting Pinner salt (VI-2) with ammonia to form d3-acetamidine (V-2), or a salt thereof:

and
c1) reacting d3-acetamidine (V-2) with bromine, thiocyanate and sodium methoxide to afford compound of Formula (IV-2); or
c2) reacting d3-acetamidine (V-2) first with sodium hypochlorite (NaOCl) and then with thiocyanate to afford compound of Formula (IV-2).

In this process, step a) conducts to the formation of a Pinner salt by a Pinner reaction. A "Pinner reaction" refers to the acid catalyzed reaction of a nitrile (here d3-acetonitrile) with an alcohol (here ethanol) to form an imino ether salt also referred to as a Pinner salt. Pinner salts are themselves reactive and undergo additional nucleophilic addition, such as with ammonia to form an amidine as in step b).

The last step may be conducted either via "bromine route" (step c1) or via "hypochlorite route" (step c2), both providing satisfying results.

As mentioned above, the final compound or the intermediates used in the processes of the invention may be in the form of salts, including acid addition and base salts.

Step a)—Formation of the Pinner Salt

In step a), the Pinner salt of Formula (VI-2) is obtained by reacting d3-acetonitrile with ethanol in presence of HCl.

In one embodiment, the Pinner salt (VI-2) is formed in step a) by bubbling HCl gas through a mixture comprising ethanol (preferably absolute ethanol) and d3-acetonitrile.

In one embodiment, HCl bubbling is conducted at a temperature lower than 15° C., preferably lower than 10° C.

In one embodiment, HCl gas is bubbled through the mixture over at least 10 hours, preferably at least 8 hours, more preferably about 6 hours.

In an embodiment, after the end of HCl bubbling, the reaction mixture is stirred at room temperature, preferably at a temperature ranging from 20° C. to 25° C.

In an embodiment, after the end of HCl bubbling, the reaction mixture is stirred for a period of time of at least 10 hours, preferably ranging from 10 hours to 24 hours, preferably from 15 hours to 20 hours, more preferably for about 16.5 hours.

In an embodiment, after completion, the reaction mixture is treated with tert-butyl methyl ether (TBME), preferably at a temperature ranging from 0° C. to 5° C., to isolate the Pinner salt (VI-2) as a solid.

Step b)—Formation of Deuterated Acetamidine

In step b), deuterated acetamidine (V-2) is formed by reacting Pinner salt (VI-2) with ammonia (NH$_3$).

In one embodiment, the solvent used in step b) is an alcohol such as ethanol or methanol; preferably ethanol; more preferably absolute ethanol.

In one embodiment, step b) is performed at a temperature lower than 10° C., preferably at a temperature ranging from 0° C. to 5° C.

In one embodiment, ammonia (NH$_3$) is used as a gas and is directly absorbed in the reaction mixture. Preferably from 3 to 5 molar equivalents of ammonia are used with respect to Pinner salt (VI-2); preferably 4.1 molar equivalents.

In one embodiment, the reaction of step b) is performed for a period of time of at least 1 hour, preferably ranging from 1 to 6 hours, preferably from 2 to 4 hours, more preferably about 3 hours.

In an embodiment, after completion, the reaction mixture is evaporated and treated with methylcyclohexane to recover d3-acetamidine (V-2) under the form of a solid.

Advantageously, d3-acetamidine (V-2) is obtained with an isotopic purity of at least 90%, preferably of at least 95%.

Step c1)—Cyclisation to Form the Thiadiazole Ring Via "Bromine Route"

The last step leading to compound of Formula (IV-2) may be performed via the "bromine route" (step c1).

In step c1), compound of Formula (IV-2) is obtained by reacting d3-acetamidine (V-2) with bromine, thiocyanate and sodium methoxide.

In one embodiment, the thiocyanate is preferably used under the form of potassium thiocyanate.

In one embodiment, sodium methoxide may be obtained by solubilising sodium in methanol.

In one embodiment, the number of molar equivalents of thiocyanate is ranging from 1 to 2.6 with respect to d3-acetamidine (V-2); preferably about 1.1 equivalent.

In one embodiment, the number of molar equivalents of sodium methoxide (NaOMe) is ranging from 2 to 5 with respect to d3-acetamidine (V-2); preferably from 3 to 3.5; more preferably about 3.1 equivalents.

In one embodiment, the number of molar equivalents of bromine (Br$_2$) is ranging from 1 to 3 with respect to d3-acetamidine (V-2); preferably from 1 to 2; more preferably about 1.5 equivalents.

In one embodiment, the solvent used in step c1) is an alcohol; preferably methanol. Preferably the solvent is dry, preferably dry methanol.

In one embodiment, step c1) is performed at a temperature lower than 10° C., preferably at a temperature ranging from 0° C. to 5° C.

In one embodiment, the reaction of step c1) is performed for a period of time of at least 1 hour, preferably ranging from 1 to 6 hours, preferably from 1 to 3 hours, more preferably about 2 hours.

In one embodiment, the product is extracted with ethyl acetate and obtained under the form of a solid.

Advantageously, the thiadiazole product (IV-2) is obtained with an isotopic purity of at least 90%.

Step c2)—Cyclisation to Form the Thiadiazole Ring Via "Hypochlorite Route"

Alternatively, the last step leading to compound of Formula (IV-2) may be performed via the "hypochlorite route" (step c2).

In step c2), compound of Formula (IV-2) is obtained by first reacting d3-acetamidine (V-2) with sodium hypochlorite (NaOCl), leading to the formation of intermediate (VIII-2), or a salt thereof:

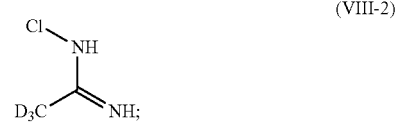

(VIII-2)

and then reacting formed intermediate (VIII-2) with thiocyanate.

In one embodiment, sodium hypochlorite (NaOCl) is used under aqueous form and may be obtained from dissolution of NaOCl pentahydrate in water.

In one embodiment, the number of molar equivalents of sodium hypochlorite (NaOCl) is ranging from 1 to 5 with respect to d3-acetamidine (V-2); preferably from 1.5 to 2.

In one embodiment, the solvent used for the reaction with sodium hypochlorite is water; preferably deionized water.

In one embodiment, the reaction with sodium hypochlorite is performed at a temperature lower than 10° C., preferably at a temperature ranging from 0° C. to 5° C.

In one embodiment, the reaction with sodium hypochlorite is performed for a period of time of at least 30 minutes, preferably ranging from 1 to 6 hours, preferably from 1 to 3 hours, more preferably about 2 hours.

In one embodiment, the resulting intermediate (VIII-2) is extracted with ethyl acetate.

In one embodiment, the thiocyanate is preferably used under the form of sodium thiocyanate.

In one embodiment, the number of molar equivalents of thiocyanate is ranging from 1 to 2 with respect to intermediate (VIII-2); preferably from 1 to 1.5; more preferably about 1.1 equivalent.

In one embodiment, the solvent used for the reaction of intermediate (VIII-2) with thiocyanate is an alcohol; preferably methanol. Preferably the solvent is dry, preferably dry methanol.

In one embodiment, the reaction of intermediate (VIII-2) with thiocyanate is performed at a temperature lower than 10° C., preferably at a temperature ranging from 0° C. to 5° C.

In one embodiment, the reaction of intermediate (VIII-2) with thiocyanate is performed for a period of time of at least 30 minutes, preferably ranging from 1 to 6 hours, preferably from 1 to 3 hours, more preferably about 1.5 hours.

In one embodiment, the product is extracted with ethyl acetate and obtained under the form of a solid.

Advantageously, the thiadiazole product (IV-2) is obtained with an isotopic purity of at least 95%.

d3-hydroxyacetamidine Route

The invention further relates to another process of manufacturing of 3-(methyl-d3)-1,2,4-thiadiazole-5-amine (IV-2):

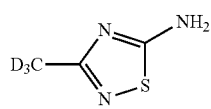

or a salt thereof,
comprising the following steps:
a) reacting d3-acetonitrile with hydroxylamine (H$_2$N—OH) to form d3-hydroxyacetamidine (IX-2), or a salt thereof:

b) performing the tosylation of d3-hydroxyacetamidine (IX-2) to form intermediate (X-2), or a salt thereof:

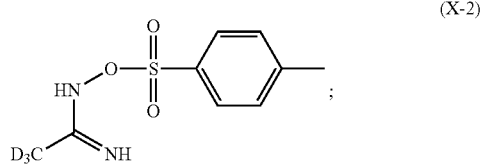 [SMILES: [2H]C([2H])([2H])C(=N)NOS(=O)(=O)c1ccc(C)cc1]

and
c) reacting intermediate (X-2) with thiocyanate to afford the compound of Formula (IV-2).

Step a)—Formation of Deuterated Hydroxyacetamidine

In step a), d3-hydroxyacetamidine (IX-2) is obtained by reacting d3-acetonitrile with hydroxylamine (H$_2$N—OH).

In one embodiment, hydroxylamine may be used under the form of aqueous hydroxylamine or hydroxylamine hydrochloride.

In one embodiment, the number of molar equivalents of hydroxylamine is ranging from 1 to 4 with respect to d3-acetonitrile; preferably from 2 to 2.5; more preferably about 2.2 equivalent.

In one embodiment, the solvent used in step a) is an alcohol; preferably ethanol.

In one embodiment, step a) is performed at reflux temperature.

In one embodiment, the reaction of step a) is performed for a period of time of at least 1 hour, preferably ranging from 1 to 24 hours, preferably about 18 hours.

Advantageously, the isotopic purity is retained during step a).

Step b)—Tosylation of Deuterated Hydroxyacetamidine

In step b), a tosylation reaction is performed on d3-hydroxyacetamidine (IX-2) to afford the corresponding tosylated intermediate (X-2). Tosylation may be performed in presence of p-toluenesulfonyl chloride and a base.

In one embodiment, the base is selected from triethylamine (TEA), sodium acetate (NaOAc), N,N-diisopropylethylamine (DIPEA), N-methylmorpholine (NMM) and mixtures thereof. In a preferred embodiment, the base is triethylamine.

In one embodiment, the number of molar equivalents of p-toluenesulfonyl chloride is ranging from 0.8 to 1.5 with respect to d3-hydroxyacetamidine (IX-2); preferably from 0.9 to 1.1; more preferably about 0.9 equivalent.

In one embodiment, the number of molar equivalents of base (such as triethylamine) is ranging from 1 to 2 with respect to d3-hydroxyacetamidine (IX-2); preferably from 1 to 1.5; more preferably about 1.3 equivalents.

In one embodiment, the solvent used in step b) is tetrahydrofuran; preferably dry tetrahydrofuran.

In one embodiment, the addition of p-toluenesulfonyl chloride is performed at a temperature lower than 10° C., preferably at a temperature ranging from 0° C. to 5° C. After completion of the addition of p-toluenesulfonyl chloride, the reaction is preferably conducted at room temperature.

In one embodiment, the reaction of step b) is performed for a period of time of at least 30 minutes, preferably ranging from 30 minutes to 3 hours, preferably about 1 hour.

In one embodiment, the product is extracted with ethyl acetate.

Advantageously, the isotopic purity is retained during step b).

Step c)—Cyclisation to Form the Thiadiazole Ring

In step c), compound of Formula (IV-2) is obtained by reacting d3-tosyloxyacetamidine (X-2) with thiocyanate.

In one embodiment, the thiocyanate is preferably used under the form of potassium thiocyanate.

In one embodiment, step c) may optionally be conducted in presence of a base. When a base is used, it may be selected from N,N-diisopropylethylamine (DIPEA), sodium acetate (NaOAc), triethylamine (TEA), N-methylmorpholine (NMN) and mixtures thereof.

In one embodiment, the number of molar equivalents of thiocyanate is ranging from 1 to 5 with respect to d3-tosyloxyacetamidine (X-2); preferably from 2 to 4: more preferably about 3 equivalents.

In one embodiment, the number of molar equivalents of base (such as DIPEA) is ranging from 0 to 2 with respect to d3-tosyloxyacetamidine (X-2); preferably from 1 to 2; more preferably from 1 to 1.5; even more preferably about 1.1 equivalents.

In one embodiment, the solvent used in step c) is selected from alcohol (such as methanol), dimethylformamide (DMF), acetonitrile, tetrahydrofuran (THF), dimethylsulfoxide (DMSO) and mixtures thereof. In one embodiment, the solvent used in step c) is methanol.

In one embodiment, step c) is performed at a temperature ranging from 20° C. to 50° C., preferably at about 40° C.

In one embodiment, the reaction of step c) is performed for a period of time of at least 1 hour, preferably ranging from 2 to 20 hours.

Advantageously, the thiadiazole product (IV-2) is obtained with an isotopic purity of at least 95%.

EXAMPLES

The present invention is further illustrated by the following examples. Reaction schemes as described in the example section illustrate by way of example different possible approaches.

Material and Methods

All reported temperatures are expressed in degrees Celsius (° C.); all reactions were carried out at room temperature (rt) unless otherwise stated.

Analytical Methods:

Analytical thin layer chromatography (TLC) was used to monitor reactions, establish flash chromatography conditions and verify purity of intermediates or final products. TLC plates used were Merck TLC aluminium sheet silica gel 60 F254. TLC plates were revealed using ultraviolet irradiation (wavelength=254 nm) at room temperature or $KMnO_4$ revelator upon heating at 160° C. The $KMnO_4$ TLC revealing agent was prepared by dissolving 3 g of potassium permanganate, 20 g of sodium carbonate in 300 mL of distilled water.

$^1H$ and $^{13}C$ NMR spectra were recorded on a Bruker Avance 500 MHz. Chemical shifts are expressed in parts per million (ppm, δ units). Coupling constants are expressed in Hertz (Hz). Splitting patterns describe apparent multiplicities and are described as s (singlet), d (doublet), t (triplet), q (quadruplet), h (heptuplet), m (multiplet), or br (broad).

GC measurements were performed on either (Conditions A) on Varian 3900 using flame ionization detector (FID) at 260° C.; the column used was an RTX-1301, 30 m×0.32 mm×0.5 µm; temperature of injector was 200° C., split ratio was 50; injected volume was 1 µl; the following temperature program was applied: oven temperature set to 60° C. for 4 min, increased linearly at a 20° C./min rate to 260° C. and maintained at 260° C. for 10 min; or (Conditions B) on Shimadzu GC-2010 using flame ionization detector (FID) at 260° C.; temperature of injector was 200° C., split ratio was 50; injected volume was 1 µl; the column used was an Rxi-17Sil MS, 30 m×0.32 mm×0.25 µm; the following temperature program was applied: oven temperature set to 60° C. for 5 min, increased linearly at a 20° C./min rate to 300° C. and maintained at 300° C. for 8 min; or (Conditions C) on Varian 3900 using flame ionization detector (FID) at 270° C.; the column used was an DB-624, 60 m×0.32 mm×3 µm; temperature of injector was 200° C., split ratio was 50; injected volume was 1 µl; the following temperature program was applied: oven temperature set to 80° C. for 4 min, increased linearly at a 20° C./min rate to 260° C. and maintained at 260° C. for 11 min.

GC-MS spectra were performed on Shimadzu GCMS-QP2010 using electron ionization detector (EI) at 250° C. The column used was a Phenomenex XB-5MS, 30 m×0.25 mm×0.25 µm. The applied column flow was 1.50 mL/min. Temperature of injector was 250° C., split ratio was 50. Injected volume was 1 µl. The following temperature program was applied: held the initial 40° C. for 5 min, then increased to 250° C. with 20° C./min, then maintained at 250° C. for 5 min.

HPLC spectra were obtained on Thermo Scientific Ultimate 3000 HPLC instrument equipped with UV detector.

Conditions A: the column used was a Phenomenex—Kinetex EVO C18 50×4.6 mm×2.6 µm. Eluent was a mixture of solution A (10 mM $HCO_2NH_4$ in $H_2O$) and solution B (MeCN). Gradient was applied at a flow rate of 1.0 mL $min^{-1}$ as follows: held the initial conditions of 1% solution B for 3 min, increased linearly to 90% solution B in 7 min, held at 90% during 2 min, returned to initial conditions in 1.0 min and maintained for 5 min. Conditions B: the column used was a Purospher Star RP18e 55 mm×4.6 mm×3.0 µm. Eluent was a mixture of solution A (20 mM $HCO_2NH_4$ in $H_2O$) and solution B (MeCN). Gradient was applied at a flow rate of 1.0 mL $min^{-1}$ as follows: held the initial conditions of 2% solution B for 1 min, increased linearly to 90% solution B in 8 min, held at 90% during 2 min, returned to initial conditions in 1.0 min and maintained for 3 min.

HPLC-MS spectra were obtained on Shimadzu LCMS-2020 using UV detection at 210 nm and Electropsray ionization (ESI). Isotopic purity determination was determined by peak area comparison for each isotope in selected ions monitoring mode.

Conditions A: the column used was a SeQuant ZIC-HILIC 150×4.6 mm×5 µm. Eluent was a mixture of 25% solution A (20 mM $NH_4Ac$ in $H_2O$) and 75% solution B (MeCN) at a flow rate of 1 mL $min^{-1}$.

Conditions B: the column used was a YMC-Triart C18 100×3.0 mm×3 µm. Eluent was a mixture of solution A (0.1% $HCO_2H$ in $H_2O$) and solution B (MeCN). Gradient was applied at a flow rate of 0.5 mL $min^{-1}$ as follows: held the initial conditions of 0% solution B for 12 min, increased linearly to 90% solution B in 5 min, held at 90% during 6 min, returned to initial conditions in 0.1 min and maintained for 7 min.

Conditions C: the column used was a Phenomenex—Kinetex EVO C18 100×2.1 mm×2.6 µm. Eluent was a mixture of solution A (0.1% $HCO_2H$ in $H_2O$) and solution B (MeCN). Gradient was applied at a flow rate of 0.5 mL $min^{-1}$ as follows: held the initial conditions of 2% solution B for 1 min, increased linearly to 90% solution B in 9 min, held at 90% during 3 min, returned to initial conditions in 0.1 min and maintained for 5 min.

Conditions D: the column used was a YMC-Triart C18 100×3.0 mm×3 µm. Eluent was a mixture of solution A (0.1% $HCO_2H$ in $H_2O$) and solution B (MeCN). Gradient was applied at a flow rate of 0.5 mL $min^{-1}$ as follows: held the initial conditions of 90% solution B for 23 min, decreased linearly to 1% solution B in 0.1 min and maintained for 7 min.

Alternatively, HPLC-MS spectra were obtained on an Agilent LCMS using electrospray ionization (ESI). The Agilent instrument includes an autosampler 1100, a binary pump 1100, an ultraviolet multi-wavelength detector 1100 and a 6100 single-quad mass-spectrometer. Conditions D: the column used was Sunfire 3.5 µm, C18, 3.0×50 mm. Eluent used was a mixture of solution A (0.1% TFA in $H_2O$) and solution B (0.1% TFA in MeCN). Gradient was applied at a flow rate of 1.3 mL per minute as follows: (for analysis of final compounds and intermediates): held the initial conditions of 5% solution B for 0.2 min, increased linearly to 95% solution B in 6 min, held at 95% during 1.75 min, returned to initial conditions in 0.25 min and maintained for 2.0 min.

Chlorine ion content was acquired using Mettler Toledo DL50 or equivalent titrator, DM-141 or equivalent electrode, an analytical balance, standard laboratory glassware. Chemicals used were titrant: 0.1 mol/L silver nitrate (preparation of 0.1 mol/L silver nitrate: weight approximately 17 g silver nitrate ($AgNO_3$) into 1000 mL volumetric flask and dissolve and dilute to volume with deionized water. Determine the factor of the solution. Sample preparation: weight 30-500 mg of solid sample in analytical balance into vessel in function of halogenide content. Dilute the samples to 60 mL with solvent. (Deionized water, 2-Propanol, etc.). Evaluation of result:

$$w/w\ \% = \frac{Q1 * M_x}{m} * 100$$

$$w/V\ \% = \frac{Q1 * M_x}{V} * 100$$

where: Q1 titrant (mmol) for equivalent point, $M_x$: molar mass (mg/mmol), m: sample weight (mg) and V: sample volume (µL)

| Halogenide | Chloride |
|---|---|
| $M_x$ (mg/mmol) | 35.45 |

Assay based on chloride ion content was calculated from the chloride assay as follows:

$$m_{UB-17363} = 97.56 \times n_{UB-17363} = 97.56 \times \frac{m_{product} \times w_{Cl^-}}{\frac{35.45}{44.07}}$$

where 97.56 g/mol is the molecular mass of compound (V-2) and 53.45 g/mol is the molecular mass of $NH_4Cl$, $m_{product}$ is the mass of the isolated HCl salt and wcl⁻ is the weight percent of chloride ion determined by titrations.

Reactants

Solvents, reagents and starting materials were purchased and used as received from commercial vendors unless otherwise specified.

The following abbreviations are used:
AMTD: 5-amino-3-methyl-1,2,4-thiadiazole
cca.: circa,
DCM: dichloromethane,
eq: equivalent(s),
EtOAc: ethyl acetate,
EtOH: ethanol,
g: gram(s),
GC: gas chromatography,
Hex: n-hexane,
HPLC: high performance liquid chromatography,
IPA: isopropylalcohol,
L: liter(s),
LCMS: liquid chromatography coupled to mass spectrometry
MeCN: acetonitrile,
MeOH: methanol,
mL: milliliter(s),
mol: mole(s)
mmol: Millimole(s),
min: minute(s),
MS: Mass spectrometry,
NMN: N-Methylmorpholine
MW: molecular weight,
NMR: nuclear magnetic resonance
rt: room temperature,
TBME: tert-butyl methyl ether,
TEA: triethylamine,
THF: tetrahydrofuran,
TLC: thin layer chromatography,
Ts: tosyl (i.e. p-toluenesulfonyl)
vol.: volume(s).

All compounds disclosed in the present application were named using ChemDraw Ultra 12© purchased from CambridgeSoft (Cambridge, MA, USA).

Example 1A: Synthesis of Deuterated d3-AMTD (IV-2) Via Acetamidine Route

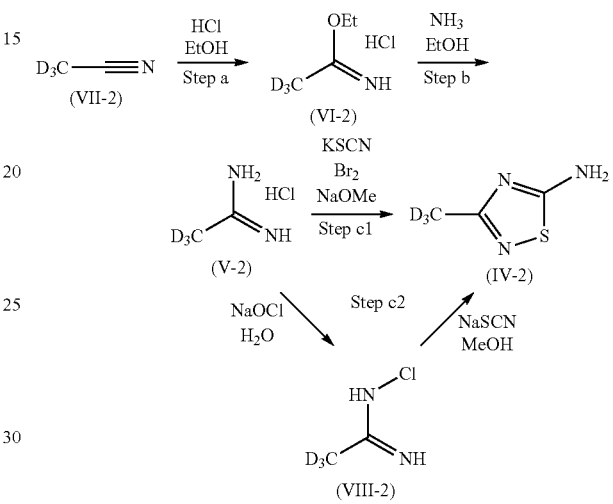

The d3-acetamidine (V-2) was obtained by Pinner reaction through Pinner salt (VI-2) before undergoing cyclization to form the thiadiazole ring of compound (IV-2), either via "bromine route" (step c1) of via "hypochlorite route" (step c2).

Step a: Formation of the Pinner Salt (VI-2)

A 750 mL, three necked glass flask equipped with two gas inlet, thermometer and magnetic stirrer at 20-25° C. was charged with: 74 mL absolute EtOH, and 51.2 g (1.161 mol, 1.0 eq) d3-acetonitrile (VII-2), then cooled to 0-5° C. (cooled by ice-salt mixture). Keeping the temperature under 10° C. HCl gas was bubbled through the mixture over 6 hours. The reaction mixture was let to warm up to 20-25° C. and stirred for 16.5 hours (the mixture became a thick, white suspension hard to stir). To the mixture, 500 mL TBME was added, then the mixture became a well stirred, white suspension. It was stirred for 1 hour at 0-5° C., then filtered, washed with 2×50 mL cold TBME. The filtered solid was dried at 40° C. under vacuum to give 104.3 g white solid Pinner salt (VI-2), which was used without further purification in the next step.

Step b: Formation of d3-Acetamidine (V-2).

A 2 L, three necked glass flask equipped with two gas inlet, thermometer and magnetic stirrer at 20-25° C. was charged with: 835 mL (658.8 g) absolute EtOH, then cooled to 0-5° C. (cooled by ice-salt mixture). At this temperature, 57.3 g (3.37 mol, 4.1 eq) $NH_3$ gas was absorbed. Then, at 0-5° C., 104.3 g (823.8 mmol, 1.0 eq) Pinner salt (VI-2) was added and stirred for 3 hours. The reaction was monitored by HPLC. The reaction mixture was evaporated until dryness at 30° C. on rotary evaporator. To the residue, 200 mL methylcyclohexane was added and stirred for 15 min at 0-5° C. (cooled by ice bath). The white precipitate was filtered, washed with 25 mL cold methylcyclohexane and dried in vacuum at 45° C. It afforded 77.1 g (790.3 mmol) white solid d3-acetamidine hydrochloride (V-2). Corrected yield: 89.3%. ¹H-NMR (DMSO-d6): δ 9.20 (br, 1H), 8.75 (br, 2H), 7.51 (br, 1H). Isotopic purity by HPLC-MS (conditions A): 95.8%. Chloride ion content: 38.46 w/w %. Assay based on chloride ion content: 93.1 w/w %

Step c1: Synthesis of d3-AMTD (IV-2) Via Bromine Route

A 250 mL, four necked glass flask equipped with two dropping funnels, thermometer and magnetic stirrer at 20-25° C. was charged with: 5.8 g (59.45 mmol, 1.0 eq.) d3-acetamidine hydrochloride (V-2) (isotopic purity: 96.5%, assay based on chloride content: 64.7 w/w %), 6.35 g (65.4 mmol, 1.1 eq.) KSCN, and 11 mL dry MeOH (dried over 4 Å molecular sieve). This mixture (suspension) was cooled below 10° C. while stirring. Keeping the temperature between 0-5° C., 42.6 mL (184.3 mmol, 3.1 eq) of 25 w/w % NaOMe solution in MeOH (54.03 g/mol) and 4.6 mL (14.26 g, 89.16 mol, 1.5 eq) Br₂ (neat, MW: 159.81 g/mol, d: 3.119 g/mL) were added simultaneously to the mixture in 25 minutes. The mixture became grey-purple then white suspension formed upon addition. After addition, the mixture was stirred for 2 hours between 0-10° C. and monitored by TLC (Eluent CH₂Cl₂: MeOH=5:1). To the mixture, 20 mL water was added gradually keeping the temperature below 25° C. The mixture was stirred for 15 minutes at ambient temperature, then 40 mL MeOH was distilled off under reduced pressure (80-120 mbar, 40° C.). The aqueous residue (around 40 mL) formed a suspension, which was filtered. The cake was washed with 3×40 mL EtOAc, obtaining 6.95 g by-product as a white solid. Each filtrate was used for extraction of the first, aqueous filtrate. The aqueous filtrate was extracted: 3×40 mL EtOAc (this is the three washing of the cake) and further 3×40 mL EtOAc. The combined organic phases were washed with 50 mL saturated NaCl solution. The extract was concentrated, at 40° C. in vacuum (100-120 mbar). The formed slurry (30 mL) was heated up and refluxed for 30 minutes, then cooled to 0-5° C. After standing at 0-5° C. overnight, the suspension was filtered and washed with 2×5 mL cold EtOAc. The product (IV-2) was obtained as an off-white solid, 1.62 g. Corrected yield: 30%. Isotopic purity: 93.4% by HPLC-MS (conditions B) and 93% by ¹H-NMR. Assay by titration: 85 w/w %. ¹H-NMR (DMSO-d6): δ 7.77 (br, 2H), 2.18 (s, 0.07H—attributed to CD2H signal).

Step c2: Synthesis of d3-AMTD (IV-2) Via Hypochlorite Route

A 500 mL, four necked glass flask equipped with two dropping funnels, thermometer and magnetic stirrer at 20-25° C. was charged with: 15.15 g (132.5 mmol, 1.0 eq.) d₃-acetamidine hydrochloride (V-2) (isotopic purity: 96.7%, assay based on chloride content: 85.7 w/w %), and 75 mL (5 vol) deionized water, then cooled to 0-5° C. Keeping the temperature between 0-5° C., 26.95 g (164 mmol, 1.24 eq) NaOCl pentahydrate dissolved in 160 mL (10.5 vol) water was added to the reaction mixture over 40 minutes. The reaction was monitored with TLC (CH₂Cl₂:MeOH=5:1). Another amount of reagent was added after 1 hour stirring: keeping the temperature between 0-5° C., 13.48 g (82 mmol, 0.62 eq) NaOCl pentahydrate dissolved in 80 mL (5.25 vol) water was added. The mixture was stirred for 1 hour at 0-5° C. Then, to the aqueous mixture, 85 g NaCl was added, then extracted with 3×200 mL EtOAc, then dried over Na₂SO₄, filtered and evaporated in vacuo (at 40° C. 10 mbar). Intermediate (VIII-2): 10.0 g red oil.

Then, a 500 mL, four necked glass flask equipped with two dropping funnels, thermometer and magnetic stirrer at 20-25° C. was charged with: 10.0 g intermediate (VIII-2) and 100 mL dry MeOH (dried over 4 Å molecular sieve), then cooled to 0-5° C. To this solution carefully was added over 20 minutes 11.75 g (145.5 mmol, 1.1 eq) NaSCN. The composed suspension was stirred for 1.5 hour, then quenched with 60 mL water. Then, the reaction mixture was filtered then the MeOH was evaporated off at 40° C. in 100-200 mbar vacuum. The residue (80 mL) was filtered, the precipitate was washed with 3×100 mL EtOAc. The mother liquid was extracted with each washing, then at the and with 100 ml EtOAc. The organic phases (4×100 mL) was combined and concentrated to 27 mL. This residue was reflux for 15 minutes, then cooled to 0-5° C., stand for 1 hour and filtered. The filtered material was the product. Crude: 26% (4.1 g) pale yellow solid. Corrected yield: 12% (1.93 g). HPLC (conditions B): 47 w/w %. Isotopic purity: 96.8% by HPLC-MS (conditions B). ¹H-NMR (DMSO-d6): δ 7.77 (br, 2H), 3.46 (br, 1H), 2.18 (s, 0.03H—attributed to CD2H signal).

Example 1B: Synthesis of Deuterated d3-AMTD (IV-2) Via Hydroxyacetamidine Route

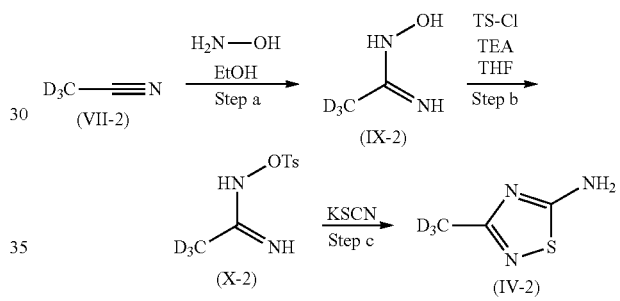

The d3-hydroxyacetamidine (IX-2) was obtained from deuterated acetonitrile (VII-2). The corresponding tosylated intermediate (X-2) was then cyclized in presence of thiocyanate to form the thiadiazole ring of compound (IV-2).

Step a: Formation of d3-Hydroxyacetamidine (IX-2)

A 100 mL glass vessel equipped with reflux condenser, thermometer and magnetic stirrer at 20-25° C. was charged with: 5.5 mL (4.65 g, 105.4 mmol, 1.0 eq.) d3-acetonitrile (d: 0.844 g/ml), 33 mL EtOH, and 25.1 mL (27.87 g, 422.3 mmol, 4.0 eq) aqueous hydroxylamine (50 w/w %, MW: 33 g/mol, d: 1.11 g/mL). The mixture was heated to reflux temperature and stirred for 5 hours at reflux temperature. The solvent was evaporated from the reaction mixture in vacuum at 40° C. The product (IX-2) was obtained as a white solid. Yield: 84% (6.84 g). Isotopic purity: 98.5% by HPLC-MS (conditions C). ¹H-NMR (DMSO-d6): δ 8.67 (br, 1H), 5.33 (br, 2H). ¹³C-NMR (DMSO-d6): δ 149.9, 16.3.

Step b: Tosylation of d3-Hydroxyacetamidine to Form Compound (X-2)

A 500 mL glass vessel equipped with thermometer and magnetic stirrer at 20-25° C. was charged with: 6.3 g (81.74 mmol 1.0 eq.) d3-hydroxyacetamidine (IX-2), 170 mL (151 g) dry THE (from molecular sieve). The mixture was stirred for 30 minutes at ambient temperature, then 14.8 mL (10.75 g, 106.3 mmol, 1.3 eq) TEA was added at 20-25° C. After 30 minutes stirring, 45 mL dry THE was added, but some undissolved material left in the mixture. The mixture was cooled to 0-5° C. by an ice-salt bath, then in several portions 14.02 g (73.57 mmol, 0.9 eq) p-toluenesulfonyl chloride was added to the mixture over 15 minutes. After addition the mixture was let warm up to 20-25° C. by removal of the cooling bath and stirred for an hour at 20-25° C. The mixture became a white suspension. Monitoring: TLC:CH$_2$Cl$_2$: MeOH=95:5. After completion (consumption of the p-toluenesulfonyl chloride), the precipitate (9.9 g white solid) was filtered off, washed with 2×40 mL THF. The filtrate was evaporated until dryness at 40° C. in vacuo. To the residue, 130 mL (118 g) EtOAc was added, the organic phase was washed with 1×65 mL water and 1×65 mL saturated aq. NaCl solution. After aqueous wash the organic layer was dried over Na$_2$SO$_4$, filtered, washed with 2×20 mL EtOAc. The solvent was evaporated in vacuo at 40° C. to give a colorless oil, which solidified upon standing. Yield: 84% (15.9 g, 68.88 mmol). Isotopic purity was retained (98.5% by HPLC-MS (conditions C)).

Step c: Synthesis of d3-AMTD (IV-2)

A 100 mL glass vessel equipped with thermometer and magnetic stirrer at 20-25° C. was charged with: 6.39 g (65.76 mmol, 3.0 eq) KSCN, 25 mL (19.8 g) dry MeOH (over molecular sieve). During stirring, 5.06 g (21.92 mmol, 1.0 eq) d3-N-tosyloxyacetamidine (X-2) was added to the mixture as a solid. After 5 minutes stirring at 20-25° C., 4.2 mL (3.12 g, 24.11 mmol, 1.1 eq) DIPEA was added. The reaction mixture was stirred at 20-25° C. overnight and became gradually a white suspension. Monitoring: TLC: CH$_2$Cl$_2$:MeOH=95:5, visualized by KMnO$_4$. The reaction was not complete after 18 hours, then it was heated to 40° C. and stirred for 2 hours. Then, the precipitate (white solid) was filtered off, washed with 2×20 mL MeOH. To the filtrate, 30 mL water was added, then the MeOH was evaporated at 40° C. in vacuo (100-150 mbar). The aqueous residue was extracted with 7×50 mL EtOAc, the combined organic phases were dried over Na$_2$SO$_4$, then evaporated. The crude product was 4.2 g orange oil. After treatment with 10 mL CH$_2$Cl$_2$, 700 mg sticky precipitate was filtered, which was treated with 5 mL iPrOAc, from which the product was isolated as 173 mg pale yellow solid (crude yield: 7%). Assay: 63 w/w % by HPLC (Conditions B). %. Isotopic purity: 73% by HPLC-MS (conditions B) The mother liquids of CH$_2$Cl$_2$ and iPrOAc treatment were combined and evaporated in vacuo at 40° C. to give 2.55 g sticky, orange solid. Assay: 10 w/w % by HPLC (Conditions B). For the whole reaction, corrected yield: 14.5% (assay 0.109 g+0.255 g).

Example 2: Synthesis of Deuterated 3-(methyl-d3)-1,2,4-thiadiazole-5-carbohydrazide (I-2)

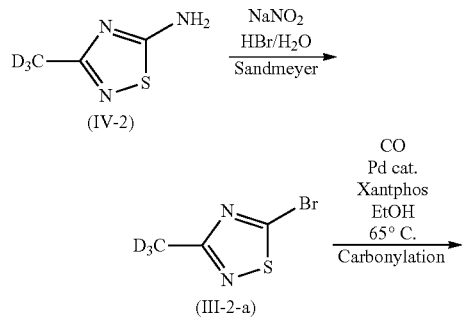

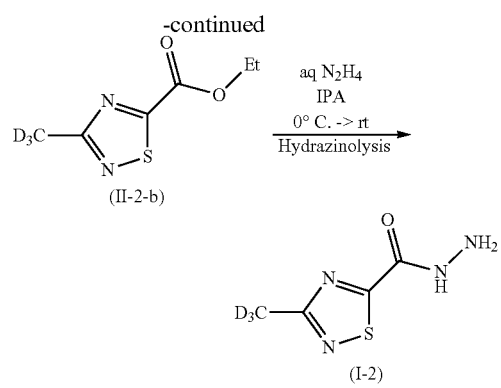

Isotopic purity was retained in all the steps.

Step 1: Sandmeyer Bromination Leading to (I-2-a)

A 25 mL glass vessel equipped with gas outlet leading to a gas trap filled with 10 w/w % NaOH solution, dropping funnel, thermometer and magnetic stirrer at 20-25° C. was charged with: 2.7 mL (4.61 g solution containing 2.85 g HBr, 35.2 mmol, 3.0 eq.) of 62 w/w % HBr solution (d: 1.702 g/mL), 2.1 mL water, and 1.39 g (11.76 mmol, 1 eq.) of compound (IV-2) (isotopic purity: 93.4%, assay by titration: 85%). The mixture was heated up to 40° C. Then, from the dropping funnel: 1.22 g (17.64 mmol, 1.5 eq.) NaNO$_2$ dissolved in 2 mL water was added at a rate to keep the temperature between 40-45° C. (in 5 minutes). During addition a brown gas composed, intensive gas bubbling was observed in the absorber and an oil phase separated at the bottom of the flask. After addition the mixture was stirred for 1 hour and monitored by TLC (Hex:EtOAc=1:1) and HPLC. The reaction mixture was cooled to 20-25° C. The two phase system was extracted with 2×10 mL dichloromethane. The combined organic phase (dark brown) was washed with: 5 mL of a 5 w/w % NaOH solution. The phases were separated. The organic phase was evaporated in vacuum (300-100 mbar) at 40° C. to give 1.51 g yellow oil (III-2-a). Yield: 78% (1.51 g). GC (condition A): 94.4%. Isotopic purity by GC-MS: 93.1%. No change was observed in isotopic purity.

Step 2: Ethoxycarbonylation Leading to (II-2-b)

Under inert atmosphere, a 50 mL autoclave at 20-25° C. was charged with: 1.2 g (6.60 mmol, 1.0 eq.) of crude compound (III-2-a) (isotopic purity: 93.1%, GC: 94.9%), 12 mL (10 vol.) dry ethanol, and 706 mg (8.58 mmol, 1.3 eq.) NaOAc. Then, nitrogen gas was bubbled through the mixture, then 19 mg (0.033 mmol, 0.005 mol eq.) Xantphos, and 7.5 mg (0.033 mmol, 0.005 mol eq.) Pd(OAc)$_2$ were added. The flask was closed, purged with nitrogen four times, then purged with CO four times, then filled with CO to 4 bar. During intensive stirring the mixture was heated to 65° C. The reaction was kept at 65° C., while the pressure was kept at 4 bar until the reaction was complete (~45 hours). The reaction was monitored by GC. After removal of the CO, and purge with nitrogen, the solvent was removed in vacuum at 40° C., then 15 mL methylcyclohexane was added, the precipitate was filtered and washed with 5 mL methylcyclohexane. The solvent was removed on rotary evaporator at 40° C. in vacuum (10 mbar). After this work-up, the product (II-2-b) was isolated as green oil. It was used in the next step without further purification. Yield: 52% (706 mg). GC (Condition A): 81%. Isotopic purity by LCMS (Condition C): 93.4%. $^1$H-NMR (DMSO-d6): δ 4.43 (q, J=7.1 Hz, 2H), 1.34 (t, J=7.1 Hz, 3H). $^{13}$C-NMR (DMSO-d6): δ 179.0, 175.9 (d), 158.4, 63.3, 18.2 (h), 14.3. No decrease was observed in isotopic purity.

Step 3: Hydrazinolysis Leading to (I-2)

A 10 mL glass vessel equipped with dropping funnel, thermometer and magnetic stirrer at 20-25° C. was charged with: 4 mL IPA and 177 µL (181 mg containing 100 mg, 3.11 mmol, 1.14 eq.) hydrazine hydrate (55 W/w % in water, d: 1.027 g/mL). The reaction mixture was cooled to 0° C. To the mixture, a solution of 595 mg (2.73 mmol, 1.0 eq.) of compound (II-2-b) (isotopic purity: 93.4%, GC: 81%) in 2 mL IPA was added from the dropping funnel at a rate to keep the temperature between 0-5° C. After addition, the mixture was stirred at 0-5° C. for an hour, then overnight at room temperature. The reaction was monitored by HPLC. After completion the suspension was cooled to 0-5° C., then filtered, the cake was washed with 2×1 mL cold IPA and dried in vacuum at 35° C. After this work-up, the product (I-2) was isolated as a pale yellow solid. Yield: 72% (321 mg). HPLC-MS (Condition D): 96.4%. Isotopic purity by HPLC-MS (Condition C): 93.4%. $^1$H-NMR (DMSO-d6): δ 10.50 (br, 1H), 4.79 (br, 2H). $^{13}$C-NMR (DMSO-d6): δ 183.4, 175.0 (d), 157.8 (d), 18.0 (h). No decrease was observed in isotopic purity.

Example 3: Synthesis of 3-methyl-1,2,4-thiadiazole-5-carbohydrazide (I-1)

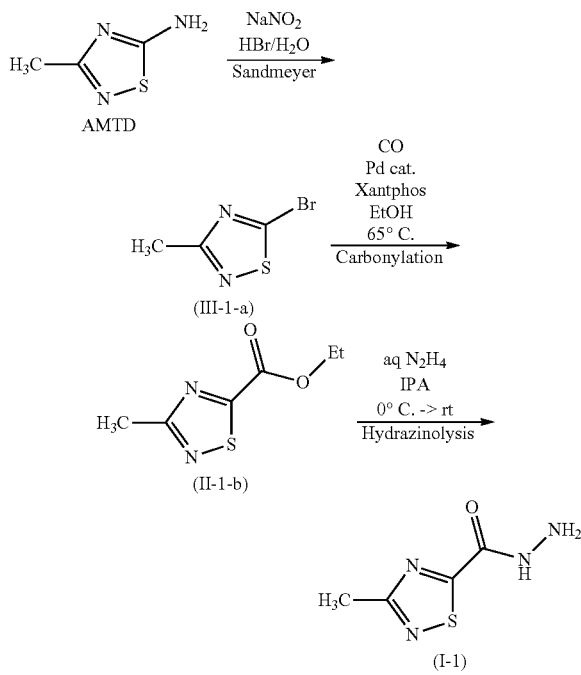

Step 1: Sandmeyer Bromination Leading to (I-1-a)

The Sandmeyer bromination procedure was successfully conducted using 100 kg of 5-amino-3-methyl-1,2,4-thiadiazole (AMTD), with a yield of 82%: 439.5 kg (295 L) 48% HBr solution and 100.0 kg AMTD are added to 54 kg (L) water in a reactor. The solution is warmed up to maximum 40° C. and stirred until all the starting material dissolves in—checking by sampling. If the starting material does not dissolve in completely, then 2 hours stirring at 40° C. is enough. 89.7 kg sodium nitrite are dissolved in 150 kg (L) water in another equipment then the solution is loaded into a container. The sodium nitrite solution is charged to the reactor portion wise, it takes about 6 hours, keeping the temperature between 40-45° C. Sampling after one hour from the end of addition. End-point criteria: starting material<1.0%. If the starting material>1.0%, extra sodium nitrite solution (10-20%) is necessary to add to the reaction mixture. In case the reaction mixture meets the end-point criteria it is cooled down to 20-25° C. and 399.0 kg (300 L) DCM is added. After 10 minutes stirring and 10 minutes settling the lower organic phase is loaded to a container. The water phase is extracted with 133.0 kg (100 L) DCM in the reactor. The pH of combined organic phase is adjusted to 10-11 by addition of 5% sodium hydroxide solution. If the pH exceeds 11, large amount of moisture can be formed. The mixture is stirred for 20 minutes, and after 30 minutes settling the organic phase is separated to a dry equipment, and concentrated in vacuum (appr. −0.9 bar) at max 30° C. Sampling, end-point criteria for the concentration: DCM content max 5.0%. After finishing the distillation, 4-6 hours stirring in vacuum is required to reach the max 5.0% DCM content. 2.0% DCM content could be favorable in the next step. In case the material meets the end-point criteria it is filled to a PE lined barrel. (126.8 kg of compound (III-1-a) were obtained; Yield: 81.6%; GC purity (Conditions C): 97.2%.

Step 2: Ethoxycarbonylation Leading to (II-1-b)

The ethoxycarbonylation procedure was successfully conducted using 87.5 kg of compound (III-1-a), with a yield of 87%:

87.5 kg compound (III-1-a) are added to 44 kg absolute ethanol in a PE lined barrel and stirred until clear solution is obtained. 383 kg (484 L) absolute ethanol is charged to a dry, pressure-resistant equipment. After inertisation with $N_2$, solution of catalyst is added which prepared from 0.672 kg palladium (II) acetate and 1.68 kg Xantphos in 14.5 kg glacial acetic acid. 52.5 kg anhydrous sodium acetate is added to the mixture. The system is purged with $N_2$ again and the reaction mixture is warmed up to 63-67° C. The equipment is filled with CO to 4-4.5 bar then the (III-1-a) solution is feed in 2-3 hours. After the addition 16 kg (20 L) ethanol is used for rinsing. Sampling in every 12 hours, end-point criteria: Starting material (III-1-a) max 1.0%. As the reaction reaches the end-point criteria the pressure is released via CATOX catalyst and the equipment is purged with $N_2$ 6 times. The mixture is filtered to a dry container by a process filter—washed with 80 kg (100 L) absolute ethanol. The filtrate is concentrated under reduced pressure at max 50° C. The concentrate is diluted with 120 kg methyl cyclohexane and stirred for 30-40 min. The solution is filtered by a process filter that is washed with 40 kg methyl cyclohexane. The solvent is removed under reduced pressure at max 50° C. and the product is isolated by fractional vacuum distillation. (73.5 kg of compound (TI-1-b) were obtained; Yield: 87.0%; GC purity (Condition A): 96.9%.

Step 3: Hydrazinolysis Leading to (I-1)

The hydrazinolysis procedure was successfully conducted using 50 kg of compound (II-1-b), with a yield of 91%:

50.0 kg of compound (II-1-b) is dissolved in 212.2 kg (270 L) isopropyl alcohol. 26.7 kg hydrazine hydrate (55% solution in water) is added to 340 kg (432 L) isopropyl alcohol and the mixture is cooled down to 0° C. The solution of (II-1-b) is added to the cold hydrazine hydrate solution portion wise, it takes 1-2 hours, keeping the temperature between 0-5° C. After completion of the addition the mixture is stirred for additional 1 hour at 0-5° C. After 1 hour stirring check the (II-1-b) contain, if the (IT-1-b) contain>1.0%, warmed the mixture up to 20-25° C. and sampled to monitor reaction progress, Expected reaction time is 20 hours, until the end-point criteria: (II-1-b)<1.0%. In case the reaction reaches end-point criteria the suspension is cooled down to 0-5° C. and filtered. The filtered material is washed with 31.8 kg (40 L) 0-5° C. isopropyl alcohol. (37.5 kg of compound (I-1) were obtained; Yield: 91%; Purity: 99.9% by HPLC (Condition A).

Example 4: Sandmeyer Bromination Using Tert-Butylnitrite Leading to (III-1-a)

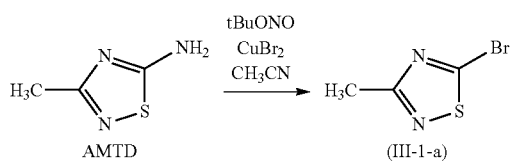

A Schlenk flask was charged with CuBr$_2$ (14 g, 62.68 mmol, 1.03 eq.), anhydrous MeCN (110 mL) and tert-butylnitrite (11 mL, 92.59 mmol, 1.5 eq.) under N$_2$, then the resulted dark green mixture was cooled between 0-5° C. (ice bath). To this mixture AMTD (7 g, 60.78 mmol, 1.0 eq.) was added portionwise over 1 min. The resulting mixture was stirred at 0-5° C. for 30 min, and then allowed to warm to rt and stirred for 2 h. The mixture was diluted with 1:1 mixture of 25% ammonia (50 mL) and 10% Na$_2$CO$_3$ (50 mL) and TBME (100 mL) was added. The phases were separated and the aqueous layer was extracted with TBME (2×50 mL). The combined organic layer was washed with brine (3×50 mL), dried over MgSO$_4$, filtered and concentrated under reduced pressure (1 mbar, 30° C.) to dryness affording compound (III-1-a) as a yellow solid in suspension in orange oil (7.16 g, 39.99 mmol, 66% yield, >98% purity by HPLC-MS (Conditions D). $^1$H-NMR (CDCl$_3$): δ 2.69 (s, 3H).

Example 5: Sandmeyer Iodination Using Tert-Butylnitrite Leading to (III-1-b)

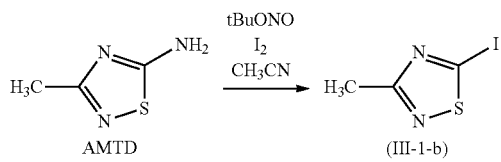

A 1000 mL three necked glass flask equipped with gas inlet, dropping funnel and thermometer was charged with 55.0 g (217.1 mmol 1.0 eq.) iodine, 250 mL dry CH$_3$CN and 102.7 mL (89.54 g, 868.4 mmol, 4.0 eq.) tBuONO. The reaction mixture was stirred for 10 minutes. At room temperature, 25.0 g (217.1 mmol, 1.0 eq.) AMTD was added as a solid in portions. After few minutes the reaction mixture (brown) started abruptly to reflux, intensive gas evolution was observed, and the reaction was cooled back to room temperature. This time (cca. 40 minutes) was enough to complete the reaction according to the TLC. The excess of iodine was quenched by the addition of 450 mL of 20 W/w % aq. Na$_2$SO$_3$, the mixture became yellow, but upon standing it became brownish again, addition of further amount of aq. Na$_2$SO$_3$ (50 mL) made the mixture yellow, but it became brownish again. The phases were separated, the aqueous phase was extracted with TBME (4×150 mL). The combined organic phase was washed with 200 mL brine, dried over Na$_2$SO$_4$, filtered and evaporated in vacuum at 30° C. The product (III-1-b) was obtained as brownish solid with 72.2% crude yield (65.7% corrected yield) (35.4 g, purity HPLC (Condition A): 92.3 area %, qNMR: 91 w/w %). The product was purified by recrystallization in refluxed 2-propanol (2 mL/crude g) with 63% yield (23.9 g, purity HPLC (Condition A): 99.3 area %, qNMR: 99 w/w %). $^1$H-NMR (CDCl$_3$): δ 2.73 (s, 3H). $^{13}$C-NMR (CDCl$_3$): δ 175.9, 124.8, 18.9.

Iodinated intermediate (III-1-b) was successfully converted in compounds (II-1-a) using the conditions of Example 3—Step 2 (CO, Pd(OAc)$_2$, Xantphos) or the conditions of Example 9 (CO, Pd(PPh$_3$)$_2$Cl$_2$).

Example 6: Sandmeyer Iodination Using Sodium Nitrite Leading to (III-1-b)

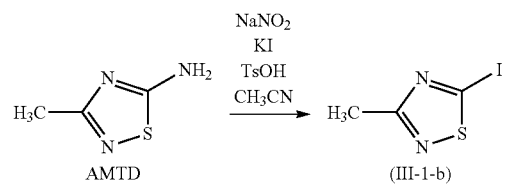

To a mixture of AMTD (58 mg, 0.50 mmol) and para-toluenesulfonic acid monohydrate (305 mg, 1.74 mmol) in anhydrous MeCN (2 mL) was added a solution of sodium nitrite (70 mg, 1.01 mmol) and potassium iodide (215 mg, 1.3 mmol) in water (0.5 mL) at 0° C. over 5 min (colourless solution turned yellow after the first drop, and then towards a black syrup, but ends up as a black solution upon end of addition). The reaction mixture was stirred at rt overnight. The reaction mixture was then diluted with NaHCO$_3$ sat. (15 mL) and extracted with EtOAc (3×10 mL). The combined organic layer was dried over MgSO$_4$, filtered and concentrated under reduced pressure (1-2 mbar, 30° C.) to dryness affording 149 mg as dark oil. HPLC-MS (Conditions D): 90 area %. $^1$H-NMR (CDCl$_3$): δ 2.73 (s, 3H). $^{13}$C-NMR (CDCl$_3$): δ 175.9, 124.8, 18.9.

Example 7: Ethoxycarbonylation Through Lithium Exchange

The introduction of the alkoxycarbonyl group on the thiadiazole may was also conducted by lithium exchange:

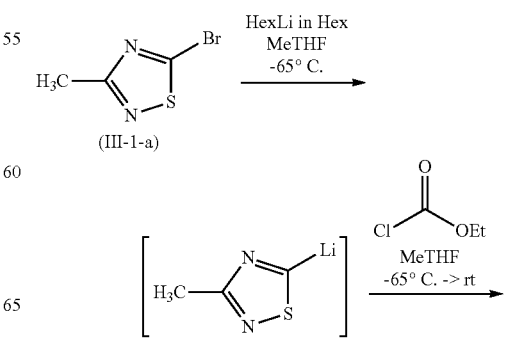

-continued

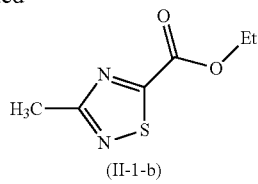
(II-1-b)

In a three necked glass vessel equipped with gas inlet, dropping funnel and thermometer 10.0 g (55.87 mmol, 1 eq) compound (III-1-a) was dissolved in 100 mL dry MeTHF under argon. The resulted mixture was cooled down to −65° C. Then 15.6 g (22.0 mL, 55.87 mmol) hexyl lithium in hexane (33%) was added dropwise during 20 min while the temperature was maintained at −65° C. After complete addition the obtained brown reaction mixture was sampled: reaction mixture+ethyl chloroformate+water+TBME. The TBME phase was analyzed by HPLC (Condition B). By in-process control, 5.5% unreacted starting material was detected, therefore 2.2 mL (5.58 mmol) hexyl lithium in hexane was added to the reaction mixture at −65° C. Twenty minutes later complete consumption of the starting bromide was detected therefore the reaction mixture was transferred via a cooled cannula into the pre-cooled mixture of 32 mL (335.16 mmol, 6 eq) ethyl chloroformate and 30 mL dry MeTHF at −65° C. during 15 min. After that the resulted dark orange reaction mixture was allowed to warm to room temperature and then 200 mL deionized water was added. The phases were separated, and the organic phase dried over $Na_2SO_4$ and concentrated to get 13.2 g brown crude product. Eight grams of the crude product was purified by vacuum distillation at 1 mbar and four fractions were collected. After distillation the collected fraction were combined and 1.9 g product (yield: 29%, HPLC purity (condition B): 92%) obtained as colorless oil. $^1$H-NMR (CDCl$_3$): δ 4.51 (q, J=7.1 Hz, 2H), 2.77 (s, 3H), 1.44 (t, J=7.1 Hz, 3H). $^{13}$C-NMR (CDCl$_3$): δ 178.8, 175.2, 158.6, 63.4, 19.1, 14.3.

Example 8: Ethoxycarbonylation with Fe(CO)$_5$

Alkoxycarbonylation was also successfully performed in presence of Fe(CO)$_5$:

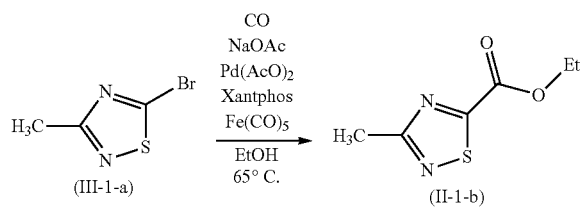

Under inert atmosphere, a 270 mL autoclave at 20-25° C. was charged with: 5.0 g (28.0 mmol, 1.0 eq.) crude compound (IIH-1-a) (purity: 96 w/w %, containing 3% dichloromethane), 50.0 mL (10 vol.) dry ethanol (water 256 ppm), and 3.0 g (36.55 mmol, 1.3 eq.) NaOAc (water 256 ppm). Nitrogen was bubbled through this mixture for 5 minutes, then 80.0 mg (0.14 mmol, 0.005 mol eq.) Xantphos, 31.5 mg (0.14 mmol, 0.005 mol eq.) Pd(OAc)$_2$ and 376 μL (560 mg, 2.86 mmol, 0.1 eq) Fe(CO)$_5$ (d: 1.45 g/mL) were added. The flask was closed, purged with nitrogen four times, then purged with CO four times, then filled with CO to 4 bar. During intensive stirring the mixture was heated to 65° C. The pressure reached 5 bar during heating. The reaction was kept at 65° C., while the pressure was kept at 4 bar until the reaction was complete (~24 hours). The reaction was monitored by GC (Condition A), Sampling: 0.4 mL reaction mixture diluted with 3.6 mL EtOH). Conversion by GC: after 17.5 h: 59%, after 24 h: 84.5%.

Example 9: Ethoxycarbonylation with Pd(PPh$_3$)$_2$Cl$_2$ Catalyst

Alkoxycarbonylation was also successfully performed in presence Pd(PPh$_3$)$_2$Cl$_2$ as catalyst.

Alkoxycarbonylation on Brominated Intermediate (III-1-a)

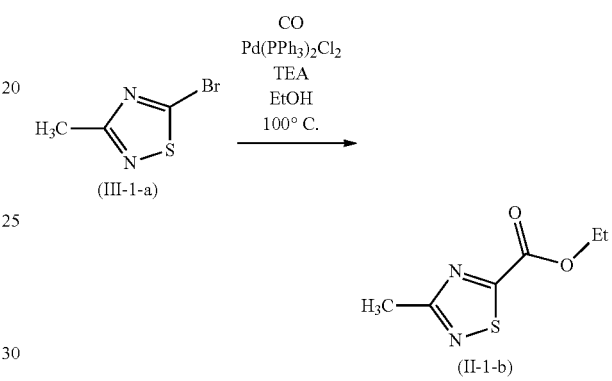

Under inert atmosphere 800 mL autoclave with magnetic stirring at 20-25° C. was charged with: 5.0 g (27.9 mmol, 1.0 eq.) distilled (IIT-1-a), 140 mL (28 vol) dry ethanol, and 5 mL (3.64 g, 35.9 mmol, 1.28 eq.) TEA. This mixture was purged with nitrogen for 10 minutes, then 1.0 g (1.42 mmol, 0.05 eq.) Pd(PPh$_3$)$_2$Cl$_2$ were added. The flask was closed, purged with nitrogen three times, then purged with CO three times, then filled with CO to 5 bar. During intensive stirring the mixture was heated to 100° C., while the pressure increased to 6.5 bar and it was stirred until completion (~31 hours). The reaction was monitored by LCMS (Condition B) after 8 hours, after 14 hours and after 31 hours (Sampling: 150 μL reaction mixture was filtered on Celite, washed with ethanol (2×150 μL) and used directly). Then, the reaction mixture was filtered through 5 g Celite and washed with 2×50 mL EtOH. The EtOH was evaporated from the filtrate in vacuo at 40° C. to give 12.09 g brown solid, which was suspended in 150 mL TBME. Then the organic phase was washed with 3×50 mL water, then evaporated in vacuum at 40° C. to give yellow mixture of oil and solid. Crude yield: 82.5% (3.96 g), LCMS (Condition B): 42 area %. $^1$H-NMR: estimated 66 n/n % (not taking PPh$_3$O into account).

Alkoxycarbonylation on Iodinated Intermediate (III-1-b)

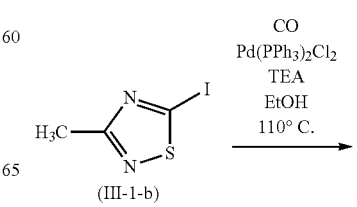
(III-1-b)

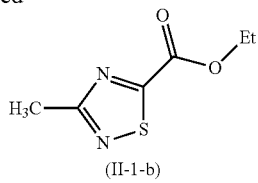

(II-1-b)

An autoclave vessel was charged with compound (III-1-b) (1 g, 4.34 mmol), TEA (0.75 mL, 5.34 mmol), dichlorobis(triphenylphosphine)palladium(II) (60 mg, 0.08 mmol) in anhydrous ethanol (20 mL). Vessel was then purged with carbon monoxide twice and pressurized to 10 bars and heated to 110° C. HPLC-MS monitoring (Conditions D) showed complete conversion in 4 h. The mixture was filtered on Celite, solids washed with EtOH (20 mL) and filtrate was concentrated under reduced pressure (1-2 mbar, 40° C.) to dryness affording a yellow orangish solid. This latter was solubilized in dichloromethane (5 mL) and TBME (15 mL) was added until a precipitate formed. This off-white solid was filtered off and washed with TBME (10 mL) and the filtrate was concentrated under high vacuum (2 mbar, 40° C.) to dryness affording 854 mg as an orange solid. Purity was estimated to 59 wt % based on $^1$H-NMR (PPh$_3$O and TEA-HI salt detected), leading to 67% corrected yield.

Example 10: Ethoxycarbonylation with Pd(OAc)$_2$-PPh$_3$ Catalyst

Alkoxycarbonylation was also successfully performed in presence Pd(OAc)$_2$-PPh$_3$ as catalyst.

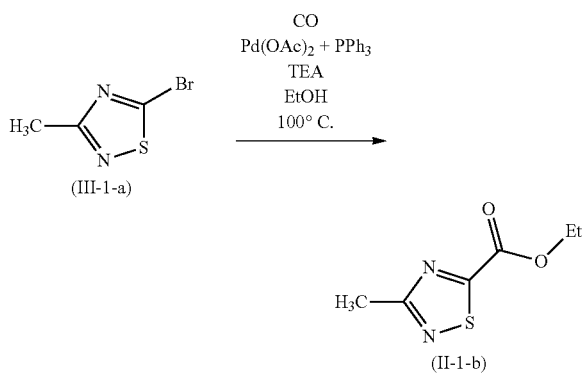

Under inert atmosphere 250 mL autoclave with mechanical stirring at 20-25° C. was charged with: 3.75 g (20.9 mmol, 1.0 eq.) distilled (III-1-a), 105 mL (28 vol.) dry ethanol, and 3.75 mL (2.73 g, 26.99 mmol, 1.29 eq.) TEA. This mixture was purged with nitrogen for 10 minutes, then 578 mg (1.05 mmol, 0.105 eq.) PPh$_3$, and 235 mg (11.17 mmol, 0.05 eq.) Pd(OAc)$_2$ were added. The flask was closed, purged with nitrogen three times, then purged with CO three times, then filled with CO to 5 bar. During intensive stirring the mixture was heated to 100° C., while the pressure increased to 6.5 bar and it was stirred until completion (~17 hours). The reaction was monitored by HPLC (Conditions B) after 17 hours (Sampling: 150 µL reaction mixture was filtered on Celite, washed with ethanol (2×150 µL) and used directly). Then, the reaction mixture was filtered through 5 g Celite and washed with 2×50 mL EtOH. The EtOH was evaporated from the filtrate in vacuum at 40° C. to give 7.03 g brown solid, which was suspended in 150 mL TBME. Then the organic phase was washed with 3×50 mL water, then evaporated in vacuum at 40° C. to give yellow mixture of oil and solid. Crude yield: 84.7% (3.05 g), LCMS (Conditions B): 71 area %. $^1$H-NMR: estimated 80 n/n % (not taking PPh$_3$O into account).

The invention claimed is:

1. A process of manufacturing of a compound of Formula (I):

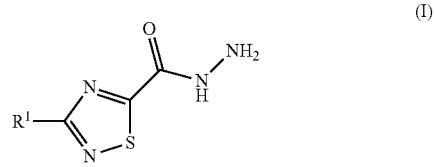

or a salt thereof, wherein R$^1$ represents methyl or methyl-d3;

said process comprising the following steps:

a) conducting an alkoxycarbonylation reaction on a compound of Formula (III):

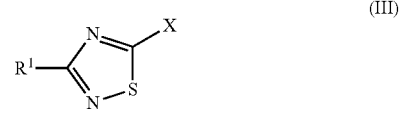

wherein X represents halo; and R$^1$ represents methyl or methyl-d3;

to obtain a compound of Formula (II):

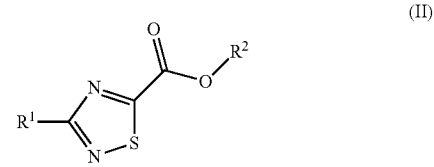

wherein R$^1$ represents methyl or methyl-d3; and R$^2$ represents alkyl or arylalkyl; and b) forming the compound of Formula (I) by reacting compound of Formula (II) with hydrazine monohydrate.

2. The process according to claim 1, wherein X represents bromo or iodo.

3. The process according to claim 1, wherein R$^2$ represents methyl or ethyl.

4. The process according to claim 1, wherein the alkoxycarbonylation reaction of step a) is performed in presence of carbon monoxide, a palladium catalyst, a base and an alcohol solvent, and optionally in presence of an organophosphorus ligand.

5. The process according to claim 4, wherein the palladium catalyst is Pd(OAc)$_2$, the organophosphorus ligand is 4,5-bis(diphenylphosphino)-9,9-dimethylxanthene (Xantphos), the base is sodium acetate and the solvent is selected from ethanol, methanol and mixtures of methyl tert-butyl ether with ethanol or methanol.

6. The process according to claim 4, wherein step a) is performed in ethanol as solvent or in a mixture of ethanol and methyl tert-butyl ether.

7. The process according to claim 1, wherein step a) is performed at a temperature ranging from 50° C. to 150° C.

8. The process according to claim 1, wherein step a) is performed in presence of Fe(CO)₅.

9. The process according to claim 4, wherein the palladium catalyst is bis(triphenylphosphine)palladium chloride (Pd(PPh₃)₂Cl₂), the base is triethylamine and the solvent is ethanol.

10. The process according to claim 1, wherein the alkoxycarbonylation reaction of step a) is performed by lithium exchange by first contacting the compound of Formula (III) with an organolithium reagent; and then adding a chloroformate or a cyanoformate.

11. The process according to claim 10, wherein the organolithium reagent is n-hexyllithium and the chloroformate is an alkyl chloroformate.

12. The process according to claim 1, comprising a preliminary step of Sandmeyer reaction on a compound of Formula (IV):

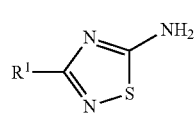

or a salt thereof, wherein R¹ represents methyl or methyl-d3;
leading to compound of Formula (III).

13. The process according to claim 12, wherein the Sandmeyer reaction is performed in presence of sodium nitrite and hydrogen bromine, in an aqueous medium.

14. The process according to claim 12, wherein the Sandmeyer reaction is performed in presence of tert-butyl nitrite and iodine or in presence of potassium iodide and p-toluenesulfonic acid.

15. A process of manufacturing of 3-(methyl-d3)-1,2,4-thiadiazole-5-amine (IV-2):

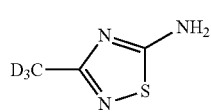

or a salt thereof,
comprising the following steps:
a) reacting d3-acetonitrile with ethanol in presence of HCl to form the Pinner salt of Formula (VI-2):

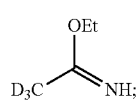

b) reacting Pinner salt (VI-2) with ammonia to form d3-acetamidine (V-2), or a salt thereof:

and c1) reacting d3-acetamidine (V-2) with bromine, thiocyanate and sodium methoxide to afford compound of Formula (IV-2); or c2) reacting d3-acetamidine (V-2) first with sodium hypochlorite (NaOCl) and then with thiocyanate to afford compound of Formula (IV-2).

16. The process according to claim 1, wherein the compound of Formula (I) is:

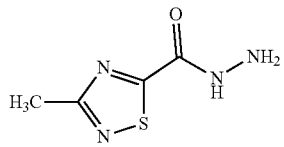

or a salt thereof;

the compound of Formula (III) is:

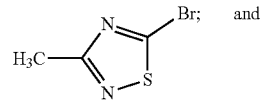

and the compound of formula (II) is:

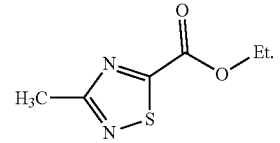

17. The process according to claim 12, wherein the compound of Formula (IV) is:

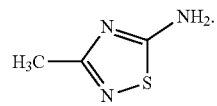

* * * * *